US006689605B1

(12) United States Patent
Mountz et al.

(10) Patent No.: US 6,689,605 B1
(45) Date of Patent: Feb. 10, 2004

(54) CONTROLLING IMMUNE RESPONSE TO SPECIFIC ANTIGENS

(75) Inventors: John D. Mountz, Birmingham, AL (US); David T. Curiel, Birmingham, AL (US); Huang-Ge Zhang, Birmingham, AL (US)

(73) Assignee: UAB Research Foundation, Birmingham, AL (US)

( * ) Notice: Subject to any disclaimer, the term of this patent is extended or adjusted under 35 U.S.C. 154(b) by 0 days.

(21) Appl. No.: 09/424,281

(22) PCT Filed: May 22, 1998

(86) PCT No.: PCT/US98/10381

§ 371 (c)(1),
(2), (4) Date: Jan. 20, 2000

(87) PCT Pub. No.: WO98/52615

PCT Pub. Date: Nov. 26, 1998

Related U.S. Application Data

(60) Provisional application No. 60/047,426, filed on May 22, 1997.

(51) Int. Cl.[7] .......................... C12N 15/63; C12N 5/00; C12N 15/00; A61K 48/00
(52) U.S. Cl. ..................... 435/320.1; 435/455; 435/325; 424/93.2; 424/93.21; 424/199.1
(58) Field of Search ............................. 435/320.1, 325, 435/455; 424/199.1, 93.2, 93.21; 514/44

(56) References Cited

U.S. PATENT DOCUMENTS

| 5,585,362 A | 12/1996 | Wilson et al. ................. 514/44 |
| 5,658,776 A | 8/1997 | Flotte et al. ............. 435/172.3 |
| 5,670,488 A | 9/1997 | Gregory et al. ................ 514/44 |

OTHER PUBLICATIONS

Miller et al.; Targeted vectors for gene therapy, 1995, FASEB J. 9: 190–199.*
Verma et al.; Gene therapy–promises, problems and prospects, 1997, Nature vol. 389: 239–242.*
Marshall; Gene Therapy's Growing Pains, 1995, Science vol. 269: 1050–1055.*
Deonarain; Ligand–targeted receptor–mediated vectors for gene delivery, 1998, Exp. Opin. Ther. Patents 8(1): 53–69.*
Orkins et. al.; Report and Recommendations of the Panel to Assess the NIH Investment in Research on Gene Therapy, 1995.*
Zhang et al. "Application of a Fas Ligand Encoding a Recombinant Adenovirus Vector for Prolongation of Transgene Expression" Journal of Virology, vol. 72, No. 3, pp. 2483–2490 (Mar. 1998).
Mineta et al. "Attenuated multi–mutated herpes simplex virus–1 for the treatment of malignant gliomas" Nature Medicine, vol. 1, No. 9, pp. 938–943 (Sep. 1995).
Andreansky et al. "Evaluation of Genetically Engineered Herpes Simplex Viruses as Oncolytic Agents for Human Malignant Brain Tumors" Cancer Research 57, pp. 1502–1509 (Apr. 15, 1997).

Muruve et al. "Adenovirus–Mediated Expression of Fas Ligand Induces Hepatic Apoptosis after Systemic Administration and Apoptosis of Ex Vivo–Infected Pancreatic Islet Allografts and Isografts" Human Gene Therapy 8, pp. 955–963 (May 20, 1997).
Rosenfeld et al. "In Vivo Transfer of the Human Cystic Fibrosis Transmembrane Conductance Regulator Gene to the Airway Epithelium" Cell, vol. 68, pp. 143–155 (Jan. 10, 1992).
Connelly et al. "In Vivo Gene Delivery and Expression of Physiological Levels of Functional Human Factor VIII in Mice" Human Gene Therapy 6, pp. 185–193 (Feb. 1995).
Bellon et al. "Aerosol Administration of a Recombinant Adenovirus Expressing CFTR to Cystic Fibrosis Patients: A Phase I Clinical Trial" Human Gene Therapy 8, pp. 15–25 (Jan. 1, 1997).
Connelly et al. "High–Level Tissue–Specific Expression of Functional Human Factor VIII in Mice" Human Gene Therapy 7, pp. 183–195 (Jan. 20, 1996).
Peng et al. "Construction of Recombinant Adeno–Associated Virus Vector Containing the Rat Preproinsulin II Gene" Journal of Surgical Research 69, 193–198 (1997).
Wagner et al. "Toward Cystic Fibrosis Gene Therapy" Annu. Rev. Med. 48:203–16 (1997).
Sata et al. "Fas ligand gene transfer to the vessel wall inhibits neointima formation and overrides the adenovirus–mediated T cell response" Proc. Natl. Acad. USA, vol. 95, pp. 1213–1217 (Feb. 1998).
Judge et al. "Functional analysis of a recombinant Fas ligand construct" Gastroenterology, vol. 112, No. 4, p. A1007 (Apr. 1997).

* cited by examiner

*Primary Examiner*—Anne M. Wehbé
(74) *Attorney, Agent, or Firm*—Gifford, Krass, Groh, Sprinkle, Anderson & Citkowski, P.C.

(57) ABSTRACT

One major problem with adenovirus gene therapy has been the T-cell mediated immune response elicited by inoculation of adenovirus, which leads to rapid clearance of the virus and loss of transgene expression. In the instant invention, the immune response to a virus is prevented by pre-treatment with adenovirus, adenoassociated virus or herpes virus infected antigen-presenting cell (APC) expressing Fas ligand with induced T-cell tolerance. Administration of AdCMVLacZ after tolerance resulted in prolonged expression of LacZ in tolerized animals compared to control treated animals. In control, but not tolerized animals, there was proliferation of $CD3^+$ T-cell in the spleen in response to AdCMVLacZ treatment. Tolerance induction is also indicated by decreased production of interferon-γ and IL-2 by peripheral T-cells isolated from treated animals after stimulation with the adenovirus infected APCs. T-cell tolerance is specific for the virus as the T-cell responses to an irrelative virus, mouse cytomegalovirus (MCMV) remained unimpaired. The instant invention utilizes virus specific T-cell tolerance, which is induced by APCs that co-express Fas ligand and virus antigens. The instant invention involves novel vectors and methods to induce tolerance to a viral vector gene therapy and prolong expression of a transgene in a viral host.

22 Claims, 13 Drawing Sheets

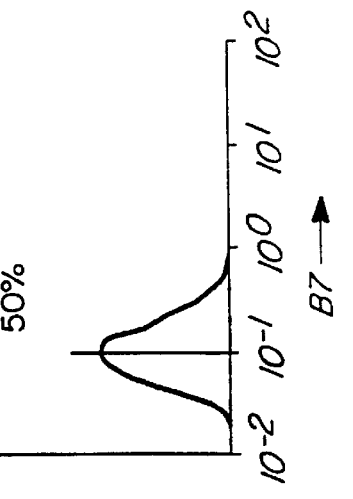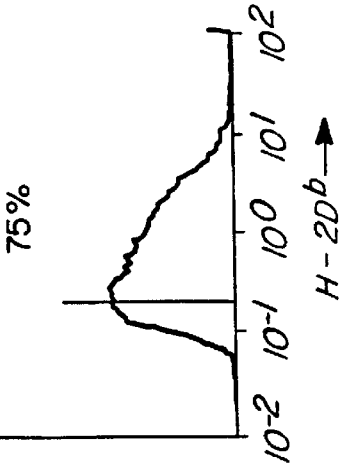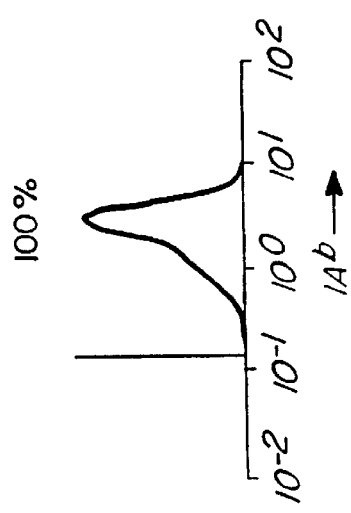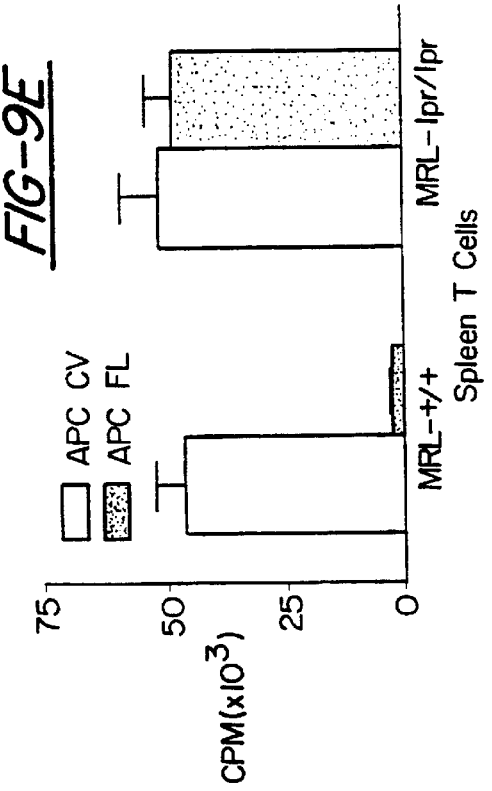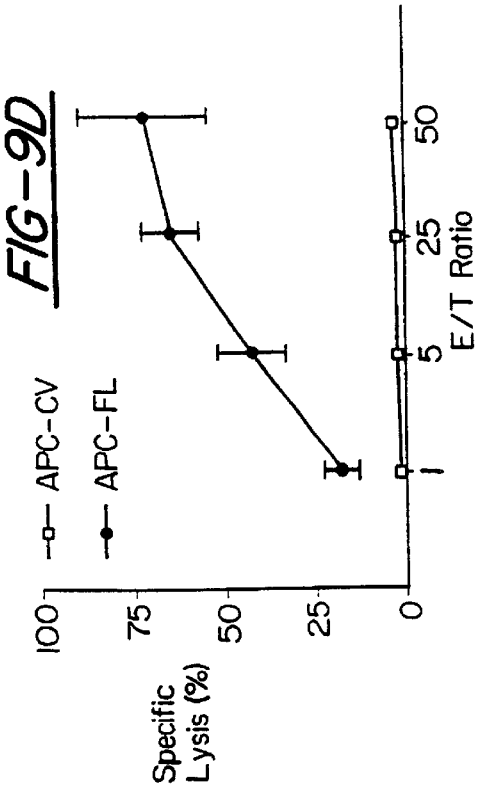

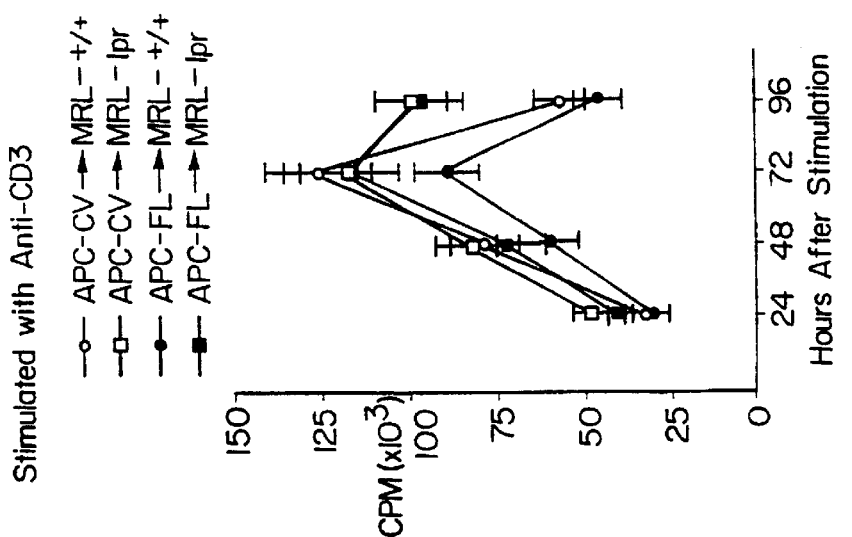
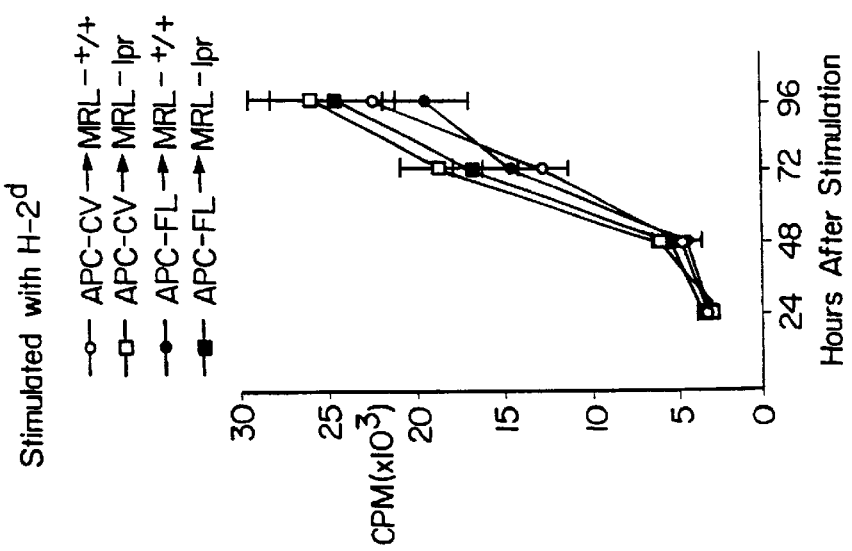
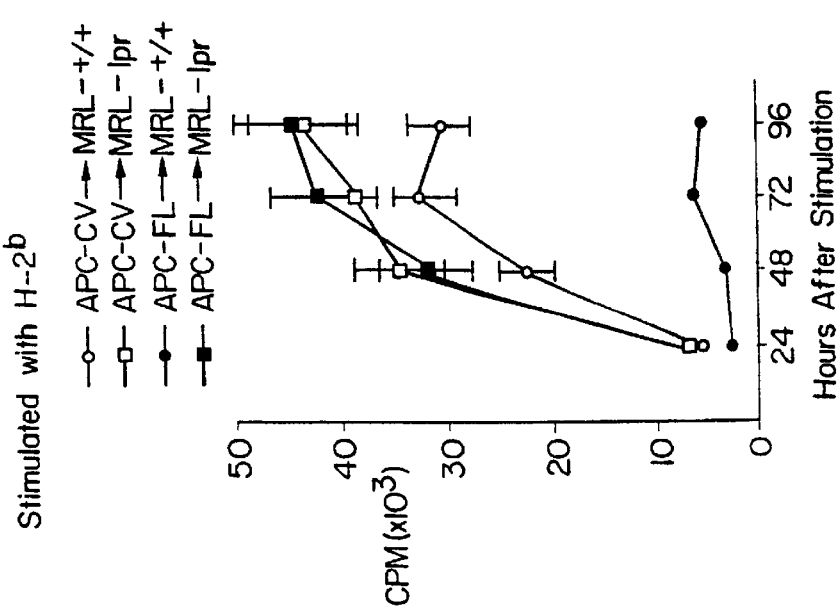

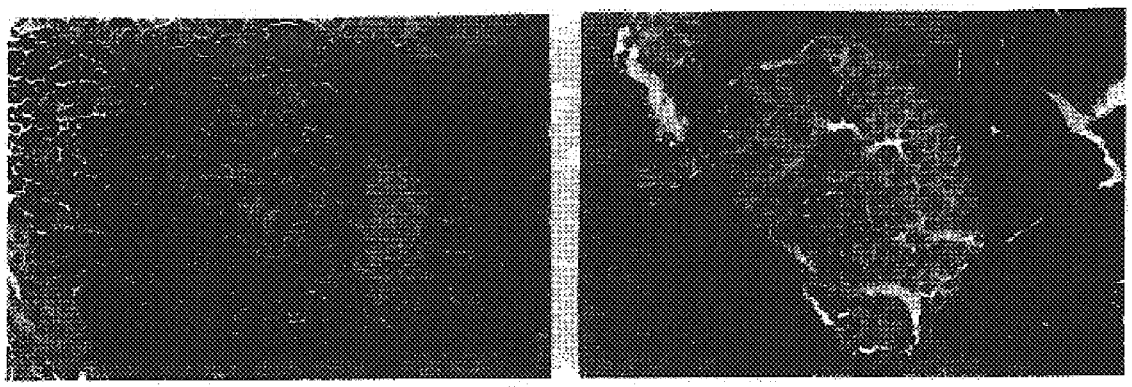
*FIG-14A*  *FIG-14B*

CONTROLLING IMMUNE RESPONSE TO SPECIFIC ANTIGENS

RELATED APPLICATION

This application claims priority of U.S. Provisional Patent Application No. 60/047,426 filed May 22, 1997 and is incorporated herein by reference.

FIELD OF THE INVENTION

This invention relates generally to gene therapy. More specifically, the invention relates to suppressing immune system response to antigens expressed on an infected host cell.

BACKGROUND OF THE INVENTION

The proper function of the immune system of an organism is to attack and neutralize materials which are perceived as being foreign to that organism. T-cells are one component of the immune system. T-cells can become activated to specific antigens, and function to directly destroy materials which display that antigen, and they also function to sensitize other components of the immune system to the presence of that antigen. While a properly functioning immune system is vital to the health of an organism, in some instances there is a need for the selective inhibition of an immune response to particular materials.

For example, viral vectors, such as adenovirus, are employed in genetic therapies to introduce genetic material and products into an organism. One problem encountered with the use of such viral vectors is that they can provoke an immune response in the organism. This immune response can destroy the viral vector, and those host cells which are intentionally infected by the vector, as well as therapeutic gene products produced by the action of the vector. Furthermore, immune system "memory" provides a lasting response to this vector; hence, readministration of the material will be ineffective. Therefore, there is a need for a method whereby the immune response to a selected viral vector may be blocked or destroyed. Suppression of immune response is also desirable in the instances of autoimmune disease. As is known, such disease results when the immune system of an organism inappropriately recognizes an organ or tissue of that organism as being foreign, and commences an immune response against it. If this immune response can be blocked, the autoimmune disease can be controlled. Immune suppression is also needed in those instances where organs are transplanted. Immune system suppressing drugs are sometimes employed in the foregoing situations; however, such drugs produce a generalized suppression of the immune system, which leaves a patient open to a number of infections. It would therefore be advantageous if immune response to a specific antigen could be suppressed and/or an immune suppressed zone of tissue created within an organism.

Gene therapy is limited by induction of an immune response to the virus or the gene-therapy protein product (1–4). A specific T-cell response to the viral vector usually results in the failure of re-expression of transgene (5–6). Many efforts have been made to reduce the T-cell response to the viral vector during gene therapy, including the blockade of MHC class I and II antigen, reduction of the antigenicity of the viral vector, and prevention of co-stimulation of T-cells (1,7–11).

One important mechanism for maintaining peripheral T-cell tolerance is clonal deletion of antigen-specific T-cells, which is mediated by apoptosis (12–15). Cytokine and cytokine ligand mediated apoptosis has been shown to be an important pathway for activation-induced cell death in T-cells (16–17). T-cell activation leads to upregulation of cytokine ligand and cytokine apoptosis signaling (18,19). Activated macrophages express increased levels of cytokine ligand and mediate apoptosis in the T-cells during antigen presentation, which has been thought to be a critical means of down-modulating T-cell response (20,21).

In particular, the efficiency of adenovirus-mediated gene transfer has been found to be far superior to other methods for the treatment of heart, lung, and liver disease, and is capable of producing more recombinant protein (22,23). However, the cell-mediated immune response to E1a-E3-deleted adenoviral (Ad5) vector and the limited distribution of reporter gene expression suggest that less immunogenic recombinant vectors and more homogeneous administration methods are required before Ad5 vectors can be used successfully for phenotypic modulation. Neonatal intrathymic injection of the vector was able to induce long-term LacZ expression for more than 2 months after heart injection, although neutralizing as well as anti-β-Gal antibodies were detected in the sera of the animals (24). Pretreatment with the anti-TCR monoclonal antibody (mAb) H57 resulted in a significant reduction in lymphocytic infiltration and a prolongation of transgene expression (25). Studies with adenoviral vectors show that immune responses limit the efficacy and persistence of gene expression. HSVtk/ganciclovir therapy was more effective in nude rats and immunosuppressed Fischer rats than in immunocompetent Fischer rats (26). The immune response against adenovirally transduced cells limits the efficacy of the HSVtk/ganciclovir system and that immunosuppression appears to be a useful adjunct. Adenoviral transgene expression was transient in the thymus of immunocompetent mice but persistent in CD8⁻ T-cell-deficient and severe combined immunodeficiency (SCID) mice, implicating a role for cytotoxic T lymphocytes in viral clearance (27). Intrathymic transplantation of syngeneic pancreatic islet cells infected with adenovirus impaired the normal antiviral cytotoxic T-lymphocyte response and prolonged hepatic transgene expression after an intravenous challenge with adenovirus.

Ad5 vector expressing the lacZ transgene, upon delivery intra-articularly ($5 \times 10^8$ p.f.u.), lacZ expression was observed in the articular synovium for at least 14 days. Anti-T-cell mAbs may be useful in inhibiting this immune response. Improved cell lines allow propagation of Ad with less genetic material, which decreases the antigenicity (28). The biologic efficacy and safety profile of second-generation adenovirus for CFTR gene was evaluated after transfer to baboon lung. This second-generation virus is deleted of E1 and contains a temperature-sensitive mutation in the E2a gene, which encodes a defective DNA-binding protein. Using a second-generation adenovirus, recombinant gene stability was prolonged and associated with a diminished level of perivascular inflammation as compared to first-generation vectors (29). These data suggest that second-generation adenoviral vectors provide an improved gene delivery vehicle and are useful in gene therapy for diseases such as cystic fibrosis.

Previous attempts to inhibit the immune response to adenovirus vector or transgenic products have all limited the utility of transgenic therapies. One technique of pre-toleration of the adenovirus is to induce neonatal toleration (30). Intratracheal administration of E1 deleted adenovirus within three days of birth resulted in transgene expression for over 6 months in cotton rats. Readministration of virus into 8 to 10 week old animals resulted in low levels of neutralizing antibodies. Later there was a T-cell response which correlated with existence of the transgene from the vector administered at birth, and also the eventual development of neutralizing antibodies (30). Neonatal administration of E1 deleted adenovirus to the small intestines also prolonged gene expression and decreased inflammatory response. Other investigators have used oral tolerance in rats to prolong gene expression and enable repeated injections lasting 100 days along with markedly inhibited lymphocyte response (31). The present invention for tolerance induction has the advantage that it does not require neonatal administration of the adenovirus.

Another mechanism of tolerance is the use of immune privileged sites. This tolerance makes use of the natural occurrence of immune privileged sites which has more recently been thought to be due to production of Fas ligand in subsequent killing of T-cells that may develop and react with antigens within these sites. Installation of adenovirus into these sites results in tolerance to adenovirus and its transgene product. This has been tested using E1 deleted adenovirus injected into this subretinal space which resulted in minimal cellular and humeral immune response (32). The pancreatic islet may also be an immune privileged sites since murine pancreatic islets injected ex-vivo with Ad5 resulted in high level of beta galactosidase for at least 20 weeks after re-implantation (33). Adenovirus mediated gene transfer in adult mouse islets does not impair insulin secretion by the islets (34). Ad lacZ injected subretinally resulted in prolonged gene expression, which was equivalent to that observed in either nude mice or after treatment with CTLA4Ig (8). The present invention is more widely applicable since transgene expression is not restricted to immune privileged sites.

SUMMARY OF THE INVENTION

In the instant invention antigen presenting cells (APCs) that express apoptosis inducing ligands and processed viral vector antigens are utilized to directly induce apoptosis of T-cells expressing the ligand receptor resulting in vector-specific T-cell tolerance. High levels of ligand and vector antigens are induced in APCs by co-infection. In the case of Fas ligand (FasL) as the cytokine and adenovirus vector co-infection with AdLoxpFasL+AxCANCre, pre-treatment of recipient mice with the adenovirus-infected APCs that express Fas ligand resulted in induction of T-cell tolerance to the adenovirus. The decreased T-cell response to the viral vector is demonstrated by decreased cytokine production, decreased cytotoxic T-cell response, inhibition of clonal expansion of CD3+T-cells, and prolonged the expression of a marker transgene. Induction of T-cell tolerance to adenovirus requires expression of FasL on the APCs, and does not occur with adenovirus infected control APCs. T-cell tolerance also requires expression of Fas on the T-cells of recipient mice, since 1pr/1pr mice are not tolerized. The T-cell tolerance is virus antigen-specific as there is normal T-cell response to mouse cytomegalovirus (CMV) in tolerized mice. These results indicate that pre-tolerization with syngeneic APCs co-infected with AdLoxpFasL +AxCANCre is a novel immunointervention strategy for tolerance induction to adenovirus gene therapy.

The instant invention includes a method for promoting immunotolerance in a host to a gene therapy vector, including transfecting a host cell with the vector, such that the vector expresses a transgene, an antigen and a ligand. Expression of the ligand induces apoptosis in a T-cell that is raised against the antigen.

The instant invention also includes a method for creating an immune privileged site in a tissue of an organism, the method including providing a gene therapy vector encoding and capable of expressing a ligand, a transgene and an antigen and infecting cells of the tissue with the vector. The expression of the ligand in the tissue thereby induces apoptosis in T-cells raised against the ligand so as to confer specific immunity to infected cells.

The instant invention also teaches a gene therapy viral vector that includes a transgene, an apoptosis ligand gene and a gene expression control means for directing product synthesis of said transgene and said ligand gene. In addition, the use of such a vector for a gene therapy application is detailed.

The instant invention also discloses a gene therapy viral vector including a transgene, a viral vector gene that is expressed as an antigen on an infected host cell, a functional equivalent of a Fas ligand gene and a gene expression control means for directing product synthesis of said transgene and said Fas ligand gene.

BRIEF DESCRIPTION OF THE DRAWINGS

FIGS. 9a–9e. Characterization of Fas ligand expressing APCs. Peritoneal resident macrophages from B6-1pr/1pr mice are isolated and cultured in RPMI-1640–12% FCS. After short-term culture, growing macrophages are tested for MHC and B7 expression. (a)–(c) $1 \times 10^6$ macrophages are stained with biotin-conjugated anti-H-2D$^b$, anti-IA$^b$ (PharMingen) or CTLA4-Ig (Dr. Linsley: Bristol-Myers Squibb), followed by FITC-conjugated streptavidin (Southern Biotechnology). 10,000 viable cells are analyzed by FACScan. (d) Macrophages are tranfected with a pcDNAIII expression vector (Invitrogen) containing a full length murine Fas ligand cDNA, or empty vector, using a standard DEAE-Dextran method. Transfected macrophages are selected with 0.5 mg/ml of G418 (Sigma). The selected macrophages are mixed with [$^{51}$C]r-labeled, Fas ligand sensitive A20 cells at the indicated ratios and, after an 8 h incubation, the specific release is determined. (e) The splenic T-cells are purified from 4wk-old MRL/MpJ-+/+ and MRL/MpJ-1pr/1pr mice (Jackson Laboratory) using a T-cell enrichment column (R&D Systems). $5 \times 10^5$ purified T-cells are cultured with $5 \times 10^4$ γ-irradiated macrophages in round-bottom, 96-well plates for 5 d, and proliferation is determined by adding 1 mCi of [$^3$H]-thymidine (Amersham) 16 h prior to harvest.

FIGS. 10A–10C. Induction of allogeneic T-cell tolerance by Fas ligand expressing APCs. 4-wk-old of MRL-+/+ and -1pr/1pr mice are injected i.v. with macrophages ($2 \times 10^5$) transfected with Fas ligand or control vector every 3 d for 6 times. On d 3 of the final injection, splenic T-cells are isolated from treated mice and cultured under various stimulatory conditions. (a) $5 \times 10^5$ T-cells are cultured with $2 \times 10^5$ γ-irradiated total spleen cells from B6+/+ mice. (b) $5 \times 10^5$ T-cells are cultured with $2 \times 10^5$ γ-irradiated total spleen cells from BALB/c mice. (c) $5 \times 10^5$ T-cells are cultured with 5 mg/ml of anti-CD3 antibody. T-cell proliferation is determined by incorporation of [$^3$H]-thymidine at indicated time points. The error bars indicate the mean ±SEM for 3 mice analyzed separately in triplicate assays.

FIGS. 14A–14B. Histologic Analysis of Insulitis. 6 wk-old female NOD mice are i.p. injected with $5 \times 10^5$ NIT-1/Ctl (A) or NIT-1/FL (B). Mice are sacrificed at 12 week of age. H&E stained paraffin sections of pancreas were examined (400×).

DETAILED DESCRIPTION OF THE INVENTION

Figure 1:
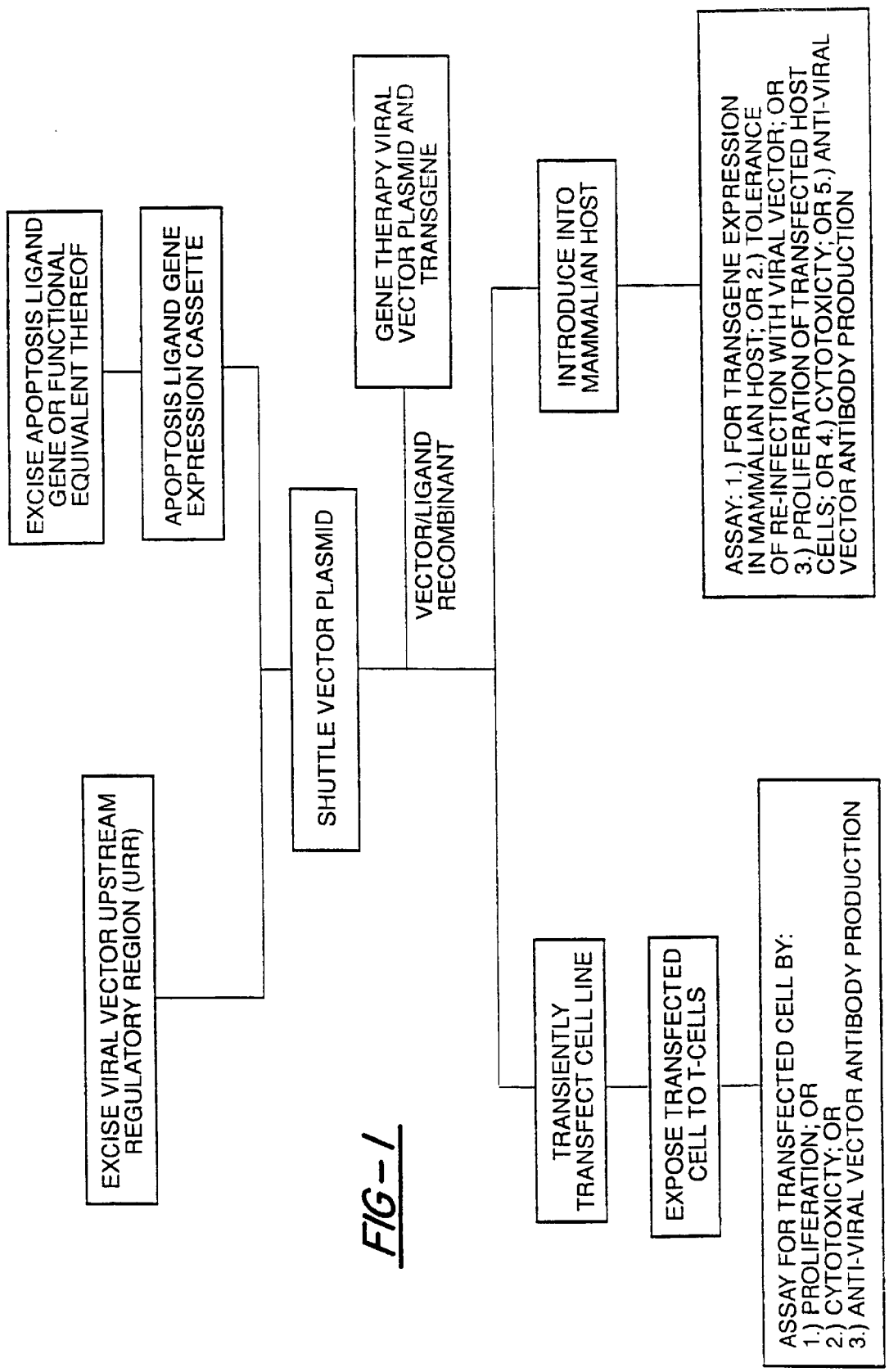
FIG. 1. A schematic illustrating a production method of gene therapy viral vector to inhibit an immune response to viral vector antigens and methods of using the same to produce immune privileged transduced mammalian host cells.

Vectors and methods are providing for introducing a transgene into a host using a virus-based delivery system, the vectors and methods designed to inhibit the host immune system from interfering with the specific gene therapy vector. The present invention incorporates the production of apoptosis inducing ligands into antigen presenting cells through gene therapy. Normally, a host T-cell directed towards an antigen of a transfected cell encounters an antigen resulting in elimination of expression of the transfecting transgene. The present invention promotes immnunotolerance towards transfected host cells. As referred to herein, the term "gene" or "transgene" is a nucleic acid, either naturally occurring or synthetic which encodes a polypeptide product. The term "nucleic acid" is intended to mean natural or synthetic linear, circular and sequential arrays of nucleotides and nucleosides, e.g. cDNA, genomic DNA, mRNA, and RNA, oligonucleotides, oligonucleosides, and derivatives thereof.

An apoptosis ligand is any polypeptide cytokine that induces apoptosis or otherwise is lethal to a cell upon complexing the ligand. Hereafter, the present invention is detailed with the exemplary naturally occurring ligand, Fas ligand; however, it is appreciated that other known apoptosis ligands are similarly operative. Other such ligands illustratively include: Fas ligand 2 which induces apoptosis by acting with death domain region molecules DR3, DR4 and DR5; TNF which induces apoptosis by acting with TNFRI; Granzyme B and porferin which are natural killing molecules associated with T-cells; and antibodies specific to T-cell apoptosis ligand receptors: anti-Fas, anti-DR3, anti-DR4, anti-DR5 and anti-TNFRI.

FIG. 1 is a schematic illustrating a production method of gene therapy viral vector to inhibit an immune response to viral vector antigens and methods of using the same to produce immune privileged transduced mammalian host cells. The method of producing an immune tolerated gene therapy vector of the present invention involves a series of steps. In selecting a virus to be modified by way of the present invention one examines a series of factors including: viral vector tropism, sites of vector expression within a host cell, ease of vector gene manipulation, required duration of expression, pathogenicity and the like. The adenovirus (Ad) affords many advantages as a vector as evidenced by its popularity. Ad replicates episomally within a host cell and as such the host cell genome is unaltered resulting in no transgene expression in host cell daughters. The adeno-associated virus (AAV) is a smaller virus than Ad. which is capable of integrating into a host cells chromosomes, thereby affords the option of long-term expression. The herpes virus (HV) is trophic for the nervous system of a host and affords the option of transducing cells of the nervous system.

Upon selection of a virus, the upstream regulatory region (URR) of the virus is excised. A URR contains at least a promoter which may be regulatable, for example, by TCN or steroids, or inducible, such as in Loxp/Cre system. The URR is closed into a shuttle vector plasmid. The shuttle vector contains an origin of replication, and an apoptosis ligand gene expression cassette. Optionally, a marker gene, an enhancer, a signal sequence, or a stuffer fragment are included in the plasmid.

An apoptosis ligand gene or fragment thereof is excised from a source cell line and cloned into an apoptosis ligand gene expression cassette. The cassette contains control elements necessary for replication within a host cell such as a promoter, a 5' untranslated region and a polyadenylation sequence. The cassette is incorporated into the shuttle vector plasmid so as to stimulate apoptosis ligand expression in concert with reading of the viral URR.

The shuttle vector plasmid is then combined with a viral vector replication plasmid from which the pathogenic protein encoding genes have been deleted or at least inactivated. The combined plasmids form a recombinant for delivering selected portions of the viral genome and an apoptosis ligand for suppressing the immune response to transfected cells presenting viral antigens thereon. FIG. 1 shows the transgene expression cassette as being incorporated into the vector replication cassette. Alternatively the transgene expression cassette is incorporated into the shuttle vector plasmid.

The recombinant is then alternatively introduced into a cell culture or into a mammalian host. The transfection of a cell culture is carried out by a prior art method (35). The transfected cells expressing viral antigens and an apoptosis ligand are identified by methods illustratively including indirect immune fluorescent assay and $^{51}$Cr release assay. Preferably, the transiently transfected antigen presenting cell lines are macrophages or NIT-1 β islet pancreas cells. It is appreciated that the present invention is readily extended to be mediated by a cell-cell interaction where the apoptosis ligand is expressed on cell type one which also expresses a different ligand, the different ligand being able to activate a receptor on a second cell type. The preferred situation is where the different ligand of cell type one—receptor of the second cell type interaction up-regulates a death domain molecule in the second cell type.

Cultured cells expressing both the ligand and viral-vector antigens are then exposed to T-cells that have been sensitized to the viral vector. The immune system challenged transfected cells are then assayed as to proliferation, or cytotoxicity or as to the inducement anti-viral vector antibody production. These assays are designed to, alone or in combination assess the extent of immuno-tolerance sensitized immune system components have towards the gene therapy vector.

The recombinant is introduced into a mammalian host by a route dictated by the targeted host cells. For instance, lung tissue to be transfected with CFTR or protease inhibitor so as to treat cystic fibrosis is preferably administered intranasally as an aerosol suspension; blood to be transfected with Factor 8 so as to treat hemophilia is preferably administered intravenously, intra peritoneally to transfect organ specific diseases of the liver, pancreas, etc., intra marrow for marrow and intra-myocardial for heart tissue It is recognized that adjuvants are readily added to a gene therapy vector of the present invention to facilitate administration. The host transfected tissues are biopsied or excreted gene product markers associated with the gene therapy are assayed to monitor the efficacy of the therapy. In vitro assays are also applicable to in vivo therapy monitoring.

The present invention provides for a gene therapy vector capable of delivering a complete apoptosis ligand, as well as smaller functional components of these ligands. Certain truncations of these ligands interact with death domain molecules and thereby induce T-cell apoptosis. For example, the nucleic acid sequences coding for Fas ligand, Fas ligand 2, Granzyme B and porferin can be altered by substitutions, additions, deletions or multimeric expression that provide for functionally equivalent ligands. Due to the degeneracy of nucleic acid coding sequences, other sequences which encode substantially the same amino acid sequences as those of the naturally occurring ligands may be used in the practice of the present invention. These include, but are not limited to, nucleic acid sequences comprising all or portions of the nucleic acid sequences encoding the above ligands, which are altered by the substitution of different codons that encode a functionally equivalent amino acid residue within the sequence, thus producing a silent change. For example, one or more amino acid residues within a sequence can be substituted by another amino acid of a similar polarity which acts as a functional equivalent, resulting in a silent alteration. Substitutes for an amino acid within the sequence may be selected from other members of the class to which the amino acid belongs. For example, the nonpolar (hydrophobic) amino acids include alanine, leucine, isoleucine, valine, proline, phenylalanine, tryptophan and methionine. The polar neutral amino acids include glycine, serine, threonine, cysteine, tyrosine, asparagine, and glutamine. The positively charged (basic) amino acids include arginine, lysine and histidine. The negatively charged (acidic) amino acids include aspartic acid and glutamic acid. Also included within the scope of the present invention are ligands or fragments or derivatives thereof which are differentially modified during or after translation, e.g., by glycosolation, protolytic cleavage, linkage to an antibody molecule or other cellular ligands, etc. In addition, the recombinant ligand encoding nucleic acid sequences of the present invention may be engineered so as to modify processing or expression of a ligand. For example, a signal sequence may be inserted upstream of a ligand encoding sequence to permit secretion of the ligand and thereby facilitate apoptosis.

Additionally, a ligand encoding nucleic acid sequence can be mutated in vitro or in vivo to create and/or destroy translation, initiation, and/or termination sequences or to create variations in coding regions and/or form new restriction endonuclease sites or destroy pre-existing ones, to facilitate further in vitro modification. Any technique for mutagenesis known in the art can be used, including but not limited to in vitro site directed mutagenesis (36), use of Tab linkers (Pharmacea), etc.

In the case of the Fas ligand, polymorphisms in the intracellular domain modify the hydrophilic regions of the ligand but do not greatly affect Fas ligand ftinction in inducing apoptosis. Thus, mutations of Fas ligand that do not affect the apoptosis inducing potential of the ligand including additions, substitutions, truncations and the like are recognized to be usable in the present invention. Indeed, a polynucleotide modification of Fas ligand to produce multimers of the Fas ligand is a means of increasing apoptosis potential of the Fas ligand. By extension, the same holds true for other ligands. It is known to the art that soluble Fas ligand binds to Fas and may impede apoptosis by endocytosis of Fas without inducing apoptosis. Therefore, larger conglomerates of Fas ligand such as surface Fas ligand or Fas ligand that has been engineered to be cross-lined and produced by cells is more affective in the induction of apoptosis than the naturally occurring Fas ligand.

In accord with the present invention, T-cells which are activated against a specific antigen, are selectively eliminated thereby preventing or reducing immune response to that antigen. T-cells are eliminated by activation-induced cell death of T-cells, which is caused by Fas-mediated apoptosis of those activated T-cells that express Fas and Fas ligand.

In the immune system, macrophages and other specialized cells, collectively referred to as antigen presenting cells (APCs), ingest antigen materials and break them into smaller peptide fragments which are presented on the surface of the APCs as a complex with major histocompatibility complex (MHC) molecules. A particular peptide/MHC complex is recognized by the specialized receptor on the surface of a T-cell thereby activating that T-cell. Activated T-cells then reproduce, and the offspring proceed to initiate an immune response by attacking those materials displaying the foreign antigen, and by further activating B cells and other components of the immune system. In addition, some of the activated T-cells persist so as to provide an enhanced response to further infection. In accord with the present invention, it has been found that immune response to a specific antigen can be very effectively blocked, if the activated T-cells, responsive to that antigen, are eliminated.

It has further been found in accord with the present invention that the Fas ligand can be employed to produce apoptosis of T-cells that express Fas. More specifically, it has been found that introduction of APCs, that express a Fas ligand, into an organism will induce apoptosis of T-cells that express Fas, thereby resulting in antigen specific T-cell tolerance. It has been found that an adenovirus capable of expressing the Fas ligand can be used to transfect macrophages and other APCs. This results in a highly efficient presentation of adenovirus antigens and Fas ligand on the APCs. Such APCs will then confer immune tolerance to the adenovirus vector by selectively eliminating those T-cells which are capable of reacting with antigens from the adenovirus vector. This novel therapeutic approach greatly enhances the utility of adenoviral based gene therapies by producing specific tolerance to the therapeutic materials. Since the therapy of the present invention is highly selective, adverse affects heretofore encountered with broad immunosuppressive approaches are eliminated.

It has further been found that adenovirus, expressing the Fas ligand, can be targeted to APCs via the mannose receptors on the APCs. APCs can be transfected with Fas, in vitro, and the transfected cells introduced into the organism; or, transfection may occur in vivo, by administration of the adenovirus vector to the organism.

Principles of the present invention are also be employed to inhibit autoimmune responses. As is known, autoimmune disease occurs when an organism's immune system becomes activated toward tissue of the organism itself. Selective apoptosis of those activated T-cells which cause the autoimmune response will control autoimmune disease. Transfection of those cells which elicit the autoimmune response with the Fas gene will produce syngeneic cells which will induce tolerance to an autoimmune antigen, in T-cells via Fas mediated apoptosis. The syngeneic cells may comprise APCs or they may comprise cells of the tissue provoking the autoimmune disease, in which instance these cells will then cause the APCs to present the Fas ligand and the autoimmune antigen.

These principles are also be employed to produce immune privileged sites within an organism. Provision of an immune privileged site facilitates organ transplant and other such tissue graft procedures. An immune privileged site also prolongs expression of an adenovirus gene product at that site. Creation of the immune privileged site is accomplished by causing cells at the site to produce the Fas ligand, and the presence of this ligand will protect an adenovirus from immune system attack. Production of Fas ligand is accomplished by the virus used for the therapy itself, or by genes introduced into the tissue via another carrier.

Fas ligand expression induces specific tolerance by apoptosis. Fas ligand expression is also induced by clonal deletion. Peripheral T-cell tolerance is maintained by activation-induced cell death of the T-cells, which is mediated by Fas-mediated apoptosis of the activated T-cells that express Fas and Fas ligand (37–41). Thus, Fas ligand expression is used to create immune-privileged sites and prevent grft rejection by inducing apoptosis in the T-cells (42–44). Transplantation of APCs expressing Fas ligand induces apoptosis of T-cells that express Fas, resulting in antigen-specific T-cell tolerance. The instant invention includes a novel immunointervention strategy for adenovirus gene therapy in which Fas ligand gene therapy is used to confer immune privilege. This response is mediated at the cell level and an immune response to cells is prevented by Fas ligand production by these cells. In one embodiment of the instant invention, the mouse FasL is introduced into the E1A site of Ad to produce a recombinant virus which is both replicative defective and expresses high levels of Fas ligand. Such a transgene vector inhibits the immune response of the host thereto, resulting in highly efficient presentation of adenovirus antigens and Fas ligand on the macrophages. This confers immune tolerance to the adenovirus gene therapy by selectively eliminating T-cells capable of reacting with adenovirus vector antigens.

The current results demonstrate that AdLoxpFasL co-infection with AxCANCre results in very high levels of FasL in a majority of infected APCs. These APCs can express high levels of Fas ligand without undergoing autocrine suicide. This is in contrast to low efficiency transfection of DNA into APCs using lipofectin (1%/–5%) orelectroporation (8%). The present invention utilizes several unique technologies to allow high expressions of Fas ligand plus high expression of process adenovirus antigen on an antigen presenting cell to induce apoptosis of T-cells that react with this antigen.

The present invention demonstrates extremely efficient inhibition of CD3$^+$ T-cell expansion that are potentially reactive with APC processed adenovinis antigens leading to prolongation of gene expression by challenge after tolerance with AdCMVLacZ. High efficiency inhibition of adenovirus-reactive T-cells is achieved by first treatment of mice with 5 dosages of APC-AdFasL using APCs from B6-1pr/1pr mice. After administration every three days with 5 dosages, these APCs tolerize to antigens for up to four weeks by inhibition of APC/antigen reactive T-cells. Therefore, administration of AdCMVLacZ ($10^{10}$ pfu.) intravenously one week after tolerance does not lead to a significant T-cell response since there is deletion or inhibition of all potentially reactive T-cells. One week after challenge with intravenous AdCMVLacZ, there was no visible expansion of CD3$^+$ T-cells in the spleen. The absence of cytotoxic T-cells at 7 days post-infection with AdCMVLacZ correlates with a prolonged expression of LacZ in toleralized mice compared to non-tolerized mice. The present invention shows that adenovirus expression of Fas ligand within an antigen presenting cell used as pretreatment can be utilized to tolerize against second administration of adenovirus/gene therapy product.

Mice are tolerized with APC-AdFas-L. There are several independently novel features to the inventive tolerance procedure. First, although direct intravenous injection of AdLoxpFasL+AxCANCre results in high co-infection of liver cells and extensive liver necrosis (45), there was no liver toxicity due to APC-Fas ligand cell therapy. Therefore, the use of APCs cell therapy results in high migration of APCs to lymphoid organs, such as the spleen, and not the liver. Second, AdCMVLacZ is used to challenge mice, but the LacZ gene is not encoded in the AdLoxpFasL+ AxCANCre viruses infecting the tolerizing APCs, since this would require a triple adenovirus infection, with potentially lower infection efficiency. Nevertheless, there is tolerance to readministration of AdCMVLacZ during challenge. AdCMVLacZ elicits an immune response to LacZ as well as adenovirus (46–48). These results indicate that tolerance to adenovirus alone can prolong gene therapy even in the absence of tolerance to one of the more immunogenic transgenes, LacZ.

Tolerance induction by APCs infected with a viral vector expressing high levels of FasL is specific for the viral vector, but not with an irrelevant virus. These results are demonstrated by tolerizing the mice with APC-AdFasL, and then challenging one week later with either AdCMVLacZ or murine cytomegalovirus (MCMV), and determining the cytotoxic response one week after challenge. There is no stimulatory response, determined by IL-2 production, after stimulation of splenic T-cells in vitro with APCs infected with AdCMVLacZ, whereas there was normal IL-2 production by T-cells from identically tolerized mice, after challenge in vivo, and stimulation in vitro with MCMV. This is significant since other methods for induction of tolerance, or immunosuppression to a viral vector gene therapy are associated with a more generalized immunosuppressed state, which would be undesirable for long-term gene therapy use. However, the present tolerizing technique completely abrogates the ability of T-cells responding to the tolerizing virus used to infect the APC, but not to APC infected with an irrelevant virus. Therefore, the present invention for tolerizing to a viral vector gene therapy is widely applicable, does not result in generalizing immunesuppression and is amenable to readministration for repeated treatment without inducing an immune-suppressed state.

Specific targeting of adenovirus to macrophages is accomplished by either of two methods. The first approach uses a method to couple the adenovirus fiber/knob to a mannosylated polylysine peptide. The modified receptor is targeted to macrophages. This technique is used to attach mannosylated polylysine to a modified, replicative defective adenovirus to determine adenovirus redirection to combine with high efficiency to APCs in vivo. These experiments show that modified adenovirus is directed to macrophages in vivo and macrophage expression of Fas ligand combined with presentation of adenovirus gene products and the desired new gene product is efficacious in prolonged expression. The result is a decrease in the initial inflammatory response to the adenovirus, along with induction of long-term T-cell tolerance, allowing for prolonged survival of cells expressing the adenovirus gene product, as well as decreased immunogenicity to the adenovirus and to the adenovirus gene product. Another method for APC infection with Ad involves using the adenovirus-polylysine infection technique to deliver adenovirus-polylysine-DNA complexes to accompany gene therapy to targeted cells for cell lines that did not already express Fas ligand. This is advantageous in the creation of immunoprivileged sites in cells that do not express Fas ligand or do not undergo apoptosis after expressing Fas ligand. This may be especially advantageous for creating immune privileged cells in vitro or for delivering to sites where low Fas expression occurs such as in the lung.

A more stringent test oftolerance induction involves later challenges of the mice in vivo with either the Ad-APC-FL or Ad-APC, as well as control Ad without APC. This subsequent reaction elicits a strong secondary immune response in the mice that were previously immunized with adenovirus, but there is little or no response in mice that have been tolerized with Ad-APC-FL. The use of the Ad-APC-FL and Ad-APC, or Ad in the subsequent administration determines if Ad-APC-FL is required with each administration of adenovirus for a specific APC, or if the initial induction of tolerance confers long-term tolerance to adenovirus. This technique is used to induce tolerance to alloantigens, and that systemic administration of APC-FL does not induce significant toxicity to the liver or long and has no other apparent toxic effect on the mouse. Thus, it may be advantageous to have continued expression of FasL by the Ad infected cell to create immune privilege sites.

Fas-ligand gene therapy is useful as a strategy to prevent immune response to viral vector antigens and in this embodiment of the invention, adenovirus. The ability to exploit this strategy is supported by the finding that Fas ligand expression can be targeted to APC in vitro using the polylysine method for targeting Fas ligand and adenovirus. This method promotes targeted gene delivery via the receptor mediator endocytosis pathway (49–53). It is necessary in this approach to link the vector, such as adenovirus to molecular conjugates and, at the same time, preserve both the binding and endosome disruption capabilities of the virus. Since fiber and penton proteins are believed to be primary responsible for binding and internalization, respectively, and hexon protein is thought to be a "scaffolding protein," the conjugates are preferably linked through the hexon protein. The linkage is accomplished by an antibody bridge through a molecular conjugate and the viral vector. This is accomplished by conjugating a monoclonal antibody against a foreign epitope on the viral vector hexon protein to the polylysine.

Preferably, the normal viral tropism of the vector is ablated. In the case of an adenoviral vector, redirection to macrophages optionally involves the mannosylated fiber-knob (53–57). Regulation of the macrophage mannose receptor expression and cloning of the mannose receptor has been carried out (58–60). The first three exons of the mannose receptor gene encode: a signal sequence, the $NH_2$-terminal cysteine rich domain, and the fibronectin type II repeat, while the final exons encode the transmembrane anchor and the cytoplasnmic tail. The intervening 26 exons encode the 8 carbohydrate-recognition domains and intervening spacer elements. The mannose receptor is expressed on alveolar macrophages and a highly homologous receptor DEC-205 is expressed on dendritic cells and thymic epithelial cells (58). DEC-205 is able to bind carbohydrates and mediate endocytosis. It is rapidly taken up into the coated pits forming vesicles and delivered to a multi-vesicular endosomal compartment that resembles the MHC class II-containing vesicles. Thus, the mannose receptor on macrophages and APCs provides an excellent target for modified adenovirus tropism and delivery of genes to APCs. The present invention preferably utilizes adenovirns expressing Fas ligand under the regulation of a well characterized target cell lysozyme promoter or a similar target specific promoter to transfect into a target cell (61–63) efficiently present of viral vector antigens and a cytokine ligand on the target cells.

EXAMPLES

Example 1
Animals.

Four to six week-old, female C57BLU6-+/+ and C57BL/6-1pr/1pr mice were obtained from the Jackson Laboratory (Bar Harbor, Mass.). Mice were maintained in pathogen free condition.

Example 2
Construct Fas Ligand Expression Adenovirus Vector.

This is carried out as previously described (45). Briefly, a 10.4 kb shuttle vector containing the fragment of adenovirus from 0 map unit to 1 map unit followed by the 1.6 kb chicken β-actin promoter plus CMV enhancer. This is followed by 2 Loxp sites separated by a Neo resistant gene plus a 0.3 kb bovine growth hormone poly A tail. The full-length 0.9 kb FasL is cloned down-stream from the bovine growth hormone poly A tail which is followed by an SV40 polyA tail and by the 9.8–16.1 map units of adenovirus.

Example 3
MCMV Virus.

MCMV Virus Smith strain is obtained from the American Type Culture Collection (Rockville, MD). The virus are titrated as duplicates in $log_{10}$ dilutions on subconfluent primary murine embryo fibroblasts in 12-well plates. Seven days later, monolayers are stained with neutral red and the number of plaques counted.

The supernatant is dispensed into aliquots, which are stored at –80° C. and used as the MCMV stock virus pool ($3 \times 10^7$ PFU/ml).

Example 4
Infection of Antigen Presenting Cells for Fas Ligand Expression.

This is carried out as previously described (45). Murine B6-lpr/lpr APCs are infected with either AdLoxpFasL plus AxCANCre (APC-AdFasL) or AdLoxpFasL plus AdCMVGFP (APC-AdControl) at 5 pfu/cell of each viruses for 1 hour at 37° C., and then infected cells continue to incubated at 37° C. for additional 24 hrs. Expressed murine FasL and adenoviral antigens on the surface of B6-lpr/lpr APCs are identified using indirect immune fluorescent assay (64) and the killing activity is evaluated by $^{5}Cr$ release assay (65).

Example 5
Analysis of FasL by APCs Infected With AdLoxpFasL Plus AxCANCre.

Fas ligand (FasL) cytotoxicity is assayed as previously described (65). FasL expression is determined by ability of the transfected APCs to induce apoptosis of a $^{51}Cr$ labeled, Fas sensitive cell line A20. Target cells ($1 \times 10^6$), which are sensitive to cytotoxic lysis, are incubated with 20 µCi of [$^{51}Cr$]-sodium chromate in 100 µl of RPMI-1640 containing 10% FCS at 37° C. for 1 h. After washing with medium, these cells are used as target cells. Effector cells are prepared from B6-lpr/lpr APCs infected with AdLoxpFasL plus AxCANCre as described above. These effector cells are then incubated with [$^{5}Cr$]-labeled target cells ($1 \times 10^4$) at different effector/target (E/T) ratios in a total volume of 200 µL of the medium. Release of $^{51}Cr$ into the supernatant is assessed 6 h later using a β-counter.

The percentage of specific $^{51}Cr$ release is calculated as follows:

$$\% \text{ specific lysis} = \frac{(\text{experimental } ^{51}Cr \text{ release} - \text{spontaneous } ^{51}Cr \text{ release})}{(\text{maximum } ^{51}Cr \text{ release} - \text{spontaneous } ^{51}Cr \text{ release})}$$

The spontaneous release of $^{51}Cr$ using these assays has routinely been 8%–12% of the maximum release.

Example 6
Administration of APC-AdFasL for Induction of Tolerance.

Ten-week-old C57BL/6-+/+ mice are injected intravenously with $1 \times 10^6$ of the APCs co-infected with AdLoxp- FasL plus AxCANCre (APC-AdFasL) or APCs co-infected with AdLoxpFasL plus AdCMVGFP (APC-AdControl) or with PBS every 3 days for 5 doses. On day 7 after the final injection, mice are challenged with AdCMVlacZ and T-cell cytotoxic response against APC+adenovirus is determined one week after challenge Example 7

Analysis of Immune Response to Adenovirus and MCMV After Tolerance.

One week after tolerance, mice are treated with AdCMVlacZ ($1\times10^{10}$ pfu i.v.) or MCMV ($1\times10^5$ pfu i.v.). After an additional 7 days, purified splenic T-cells are stimulated in vitro with APCs alone, or APCs that are incubated either with MCMV or AdCMVlacZ. After 48 hours the supernate is collected and analyzed for IL-2 and Ifn-γ expression.

Example 8

Quantitation of β-Galactosidase Expression in Liver.

β-galactosidase activity is determined as previously described (66). Freshly isolated liver tissue is homogenization for 10 s in a tissumizer in 1 ml of β-gal buffer (Tropix, Inc., Bedford Mass.). The homogenate is centrifuged at 12,500×g for 10 miin at 4° C., and the supernatant is heated for 60 min at 48° C. to inactivate the endogenous eukaryotic β-galactosidase activity. The sample is then centrifuged at 12,500×g for 5 min, and 10 μl of the supernatant is assayed for β-galactosidase activity using the Galacto-light™ (Tropix, Inc., Bedford Mass.) chemi-luminescent reporter assay. The reaction is carried out for 10 min at room temperature (RT) and β-galactosidase activity is assayed using a luminomiter (Monolight 500). The protein concentration is determined by the Bradford assay (Bio-Rad). The activity is expressed as the relative light units/min/mg of total protein in the liver.

Example 9

Analysis of Adenovirus Specific Cytotoxic T-cell Analysis Using AdCMVGFP Infected Target Cells.

The adenovirus shuttle vector construct is produced by cloning the enhanced GFP gene from pCA13 (Clonetech) into the HindIII-XbaI site. This is cotransfected with pJM17 to produce recombinant AdCMVGFP. AdCMVGFP is plaque purified by 3 rounds of selection. These are used to infect APC to be used as target cells for analysis of cytotoxic effector T-cells from mice treated with APC (AdLoxpFasL+ AdCMVGFP) and APC (AdLoxpFasL+AxCANCre). Effector cells are prepared from spleen, and peripheral lymph nodes of Ad-immunized and non-immunized mice. These effector cells are then incubated. with AdCMVGFP-infected target cells ($1\times10^5$) at different effector/target (E/T) ratios-in round-bottom-microtiter plates in a total volume of 200 μl of the medium for 48 hours, and Green fluorescent positive APC are sorted using FACS analysis. The percentage of specific cytotoxicity was calculated as follows:

$$\% \text{ specific lysis} = \frac{(100\% - \text{experimental } \% \ GFP^+ - \text{spontaneous } \% \ GFP^+)}{(100\% - \text{maximum} \% \ GFP^- - \text{spontaneous } \% \ GFP^+)}$$

Example 10

Cytokine Production in Vitro in Response to APC Infected With Adenovirus.

B6 lpr/lpr APCs are infected with AdCMVLacZ (10 pfu/cell) for 1 hour in 1 ml of media and then diluted through addition of 10 ml of RPMI1640 supplemented with 10% fetal bovine serum. The cells continue to culture at 37° C. for 24 hours. Before serving as a targeting cells, the APC is γ-irradiated, and $1\times10^5$ APC are mixed at different ratios of T-cells isolated from the spleen of tolerized mice. The mixed cells are incubated at 96 well plate for 2 days at 37° C. The supernatants are collected and induction of IL2 and interferon ganrina are determined using ELISA assay kit (R & D systems Inc., Minn.).

Example 11

Histopathological Examination of Tissue Sections.

Animals are sacrificed by cervical dislocation. Organs were removed and fixed in neutral 10% formalin/phosphate-buffered saline for 24 hr, followed by fixation in 70% ethanol for 24 hr. Tissues are then embedded in paraffin blocks, sectioned into 10 μm thickness, and stained with hematoxylin and eosin (H&E).

Example 12

Immunohistochemistry.

Paraffin-embedded tissue sections are deparaffinated and treated with 3% $H_2O_2$ at RT for 15 min. After washing 3 times with neutral phosphate buffered saline, tissues are stained with an antibody against anti-CD3 (Dako Corporation, Carpinteria, Calif.) following standard avidin-biotin conjugate (ABC) immunohistochemical techniques according to manu facturer's Smanual (Dako Corporation, Carpinteria, Calif.). A peroxidase-conjugated secondary antibody is then applied to the sections at RT for 2 h. Positive staining is visualized using diaminobenzidine (DAB) substrate (Dako Corporation).

Example 13

Statistical Analysis.

The two-tailed Student's t-test is used for statistical analysis when two different groups of samples are compared. The one factor analysis of variance (ANOVA) test is used when more than two groups of samples were compared. A p value of less than 0.05 was considered significant.

Example 14

Co-infection of AdLoxpFasL+AxCANCre Results in High Levels of FasL Capable of Inducing Apoptosis of A20 Target Cells.

Figure 2:
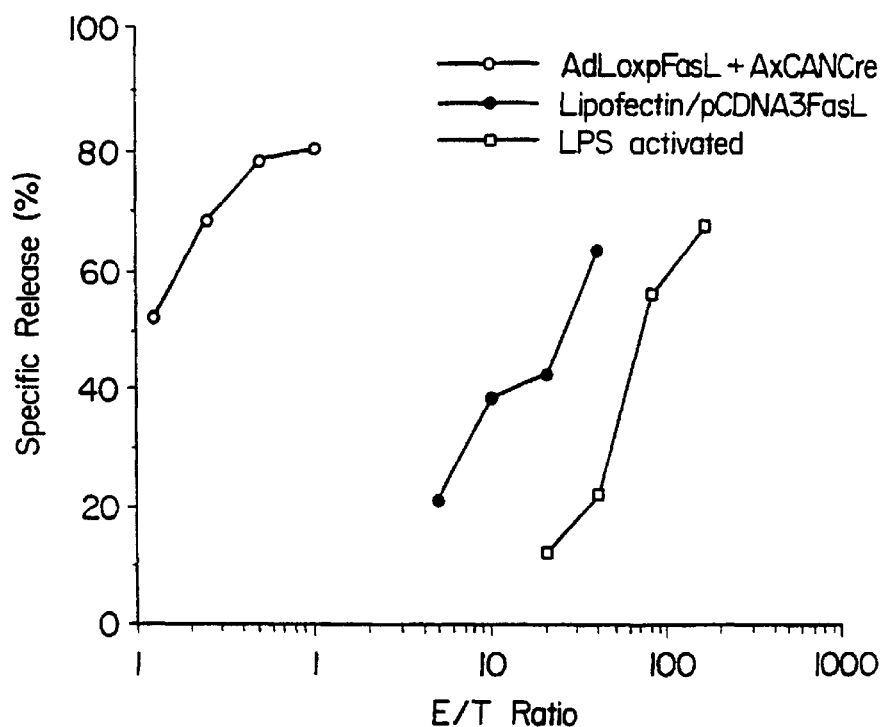
FIG. 2. Co-infection of APCs with AdloxpFasL+ AxCanCre (APC-AdFasL) results in high levels of FasL capable of inducing apoptosis of A20 target cells. The AdLoxpFasL is infected into APCs from 1pr/1pr mice with and without AxCANCre. As a comparison, the APCs are also electroporation transfected with pcDNA3FasL and stimulated with lipopolysaccharide (LPS) (1 μg/ml). FasL expression is determined by ability of the transfected APCs to induce apoptosis of a 51Cr labeled, Fas sensitive cell line A20.
Figure 3:
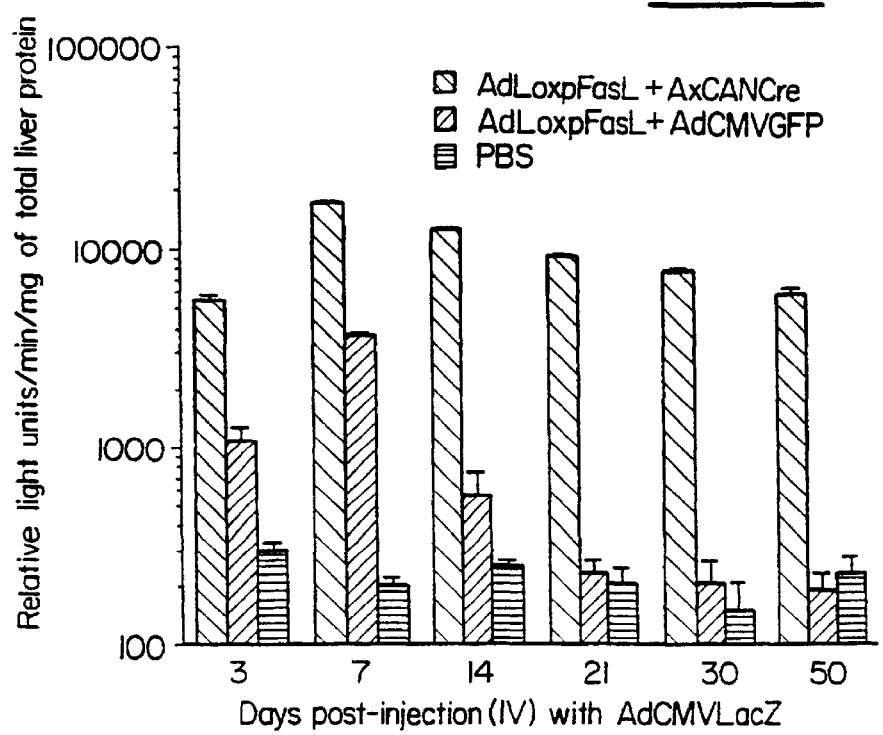
FIG. 3. Prolongation of transgene expression by Ad/FasL expressing APCs. Ten-week-old C57BL/6-+/+ mice are treated with 1×106 of the APCs co-infected with AdLoxp-FasL plus AxCANCre (APC-AdFasL) or kPCs co-infected with AdLoxpFasL plus AdCMVGFP (APC-AdControl) or PBS every 3 days for 5 doses. After induction of T-cell tolerance, mice are intravenously inoculated with 1010 Ad/LacZ. At the indicated time points, LacZ gene expression in the liver is analyzed by a quantitative assay and In situ LacZ histochemical staining. The error bars indicate the mean ±SEM for 3 mice analyzed separately in triplicate assay.

The instant invention includes an AdLoxpFasL modified adenovirus to yield high titer production of the virus in 293 cells (45). This technique also facilitates control of FasL expression since FasL is not expressed in the absence of co-infection with AxCANCre. This technique is used to induce high FasL expression by a APC cell from Fas-mutant B6-lpr/lpr mice which could induce apoptosis of A20 target cells (FIG. 2). There are very high lyses of the A20 target cells by APC infected with AdLoxpFasL+AxCANCre (APC-AdFasL) as FasL activity in APC-AdFasL is 10-fold higher compared with that of APCs transfected by electroporation with a pcDNAIII-FasL expression vector, and 100-fold higher compared to LPS-activated APCs. High levels of FasL expression by the APCs is sustained for at least 7 days of in vitro culture (FIG. 3). There is no cytotoxicity using APC+AdLoxpFasL (APC-AdControl) alone (not shown).

Example 15

Prolonged Lac Z Expression in the Liver After Tolerance With APCs/AdFasL Therapy.

Expression of adenovirus gene therapy in the liver is limited due to an acute inflammatory response and a chronic cytotoxic T-cell response (67). To determine if induction of adenoviral vector specific T-cell tolerance by AdFasL expressing APCs leads to prolongation of transgene expression delivered by adenoviral vector, the APC-AdFasL tolerized and APC-AdControl treated mice are inoculated with AdCMVlacZ (1×10$^{10}$ pfu). LacZ gene expression in the liver is kinetically analyzed by quantitative measurement of LacZ protein and histochemistry staining. The levels of LacZ gene expression in the liver rapidly decreased in mice treated with APC-AdControl (FIG. 3). In contrast, in mice treated with APC-AdFasL, the levels of LacZ gene expression is not decreased and is sustained for at least 50 days after gene delivery (FIG. 3). Histochemistry staining shows that LacZ positive cells are detectable in the liver of mice which received Ad/FasL expressing APCs at day 30 after delivery, whereas there were few LacZ positive cells in the liver which received control treatment (FIG. 3).

Example 16
Decreased Cytotoxic Response After FasL Toleration.

Figure 4:
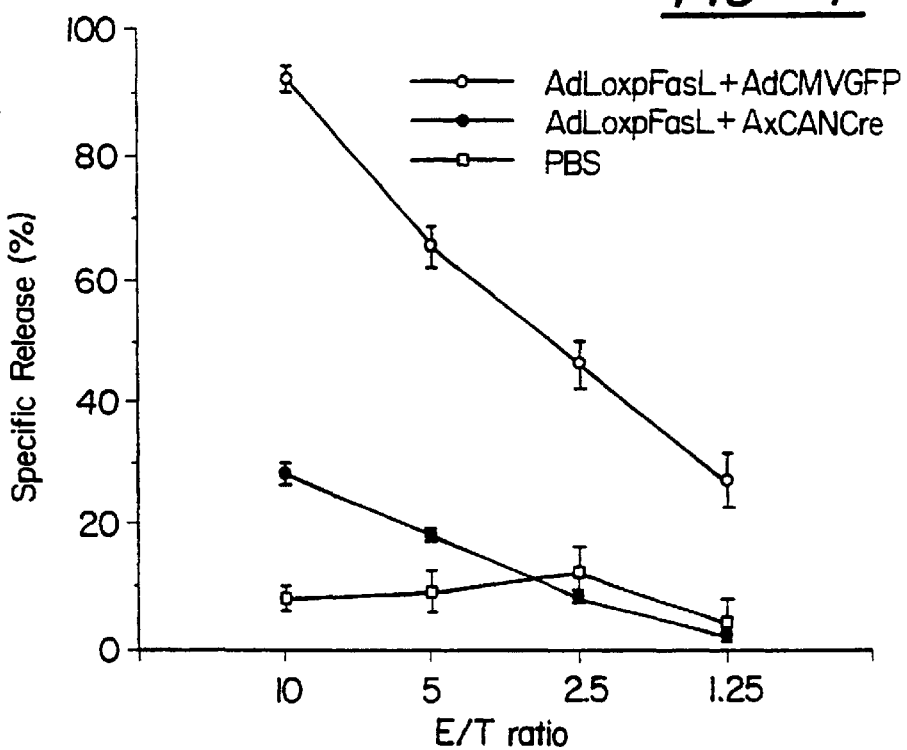
FIG. 4. Induction of tolerance to adenovirus by APC-AdFasL. Ten-week-old C57BL/6-+/+ mice are injected intravenously with 1×106 APC-AdFasL, APC-AdControl or with PBS every 3 days for 5 doses as described above. On day 7 after the final injection, mice are challenged with AdCMVlacZ and T-cell cytotoxic response against APC+ adenovirus is determined by killing of the APC cells infected with AdCMVGFP (5 pfu/cell). The percentages of viable GFP expressing APC cells are quantitated by FACS analysis. The error bars indicate the mean ±SEM for 3 mice analyzed separately in triplicate assays.

LacZ expression peaked at day 7 after expression of AdCMVLacZ in both toleralized and non-toleralized mice, and rapidly decreased in non-toleralized mice compared to toleralized after day 7. To determnine if this prolonged expression of LacZ after day 7 in the liver is associated with a decreased cytotoxic response to adenovirus, mice are toleralized in vivo as described above and challenged with AdCMVLacZ. Seven days after challenge splenic T-cells are purified and used as effect cells at different E/T ratios to kill AdCMVGFP infected APCs. There is a high cytotoxic response by T-cells from mice treated with APC-AdControl after challenged with AdCMVLacZ (FIG. 4). This is indicated by the increased killing of APC infected with AdCMVGFP. In contrast there was low cytotoxicity of mice toleralized with APC-AdFasL or PBS and challenged with AdCMVLacZ to the AdCMVGFP infected APCs.

Example 17
T-cell Tolerance Demonstrated by Decreased IFN-γ and IL-2 Production in Vivo.

Figure 5A:
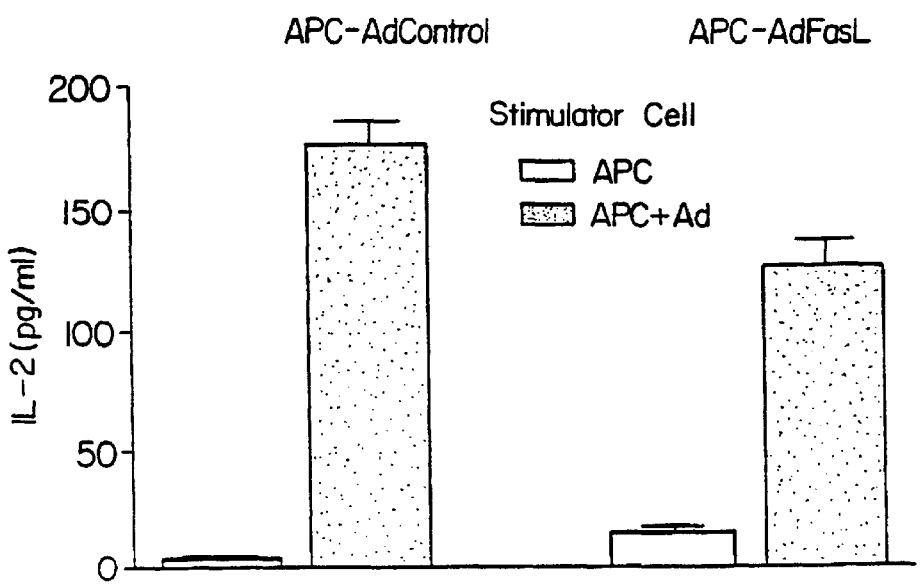
FIGS. 5A–5B. Decreased IFN-gamma and IL-2 induction by spleen cells from tolerized B6+/+ mice. $10^6$ of the APC-AdFasL or APC-AdControl cells were transferred to B6+/+ mice. The spleen cells were incubated for 24 hours with APCs that were uninfected, or infected with adenovirus, and irratiated. Levels of IL-2(A) and IFN-γ (B) in the supernatant was determined by ELISA.
Figure 5B:
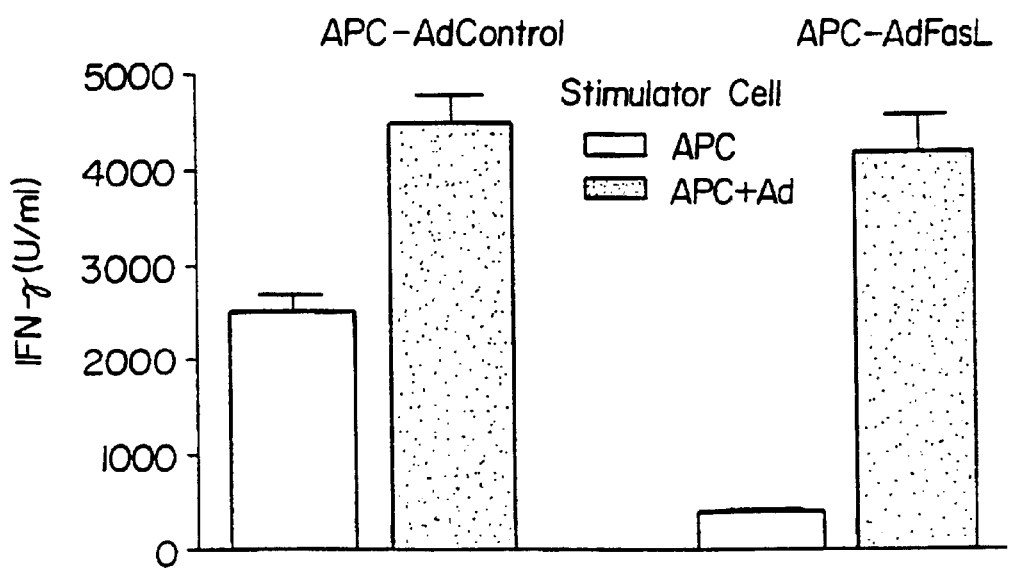

Mice are tolerized as above with either APC-AdFasL or APC-AdControl as a control. Thirty days after tolerance induction, mice are sacrificed and spleen cells are stimulated with APC or APC infected with AdCMVlacZ. Non-infected APCs did not stimulate T-cells as determnined by low IL-2 (FIG. 5A) and IFN-γ (FIG. 5B) in the supernate at 24 or 48 hours (FIG. 4). In contrast, there is high production of IL-2 and IFN-γ from spleen cells from C57BL/6 which are tolerized with APC-AdControl, which do not express FasL. B6+/+ mice that are tolerized with APC-AdFasL are tolerized as indicated by low IL-2 (FIG. 5A) and IFN-γ (FIG. 5B) in the supemate at 24 or 48 hours.

Example 18
Fas Expression by Recipient T-cells is Required for Tolerance Induction.

Figure 6:
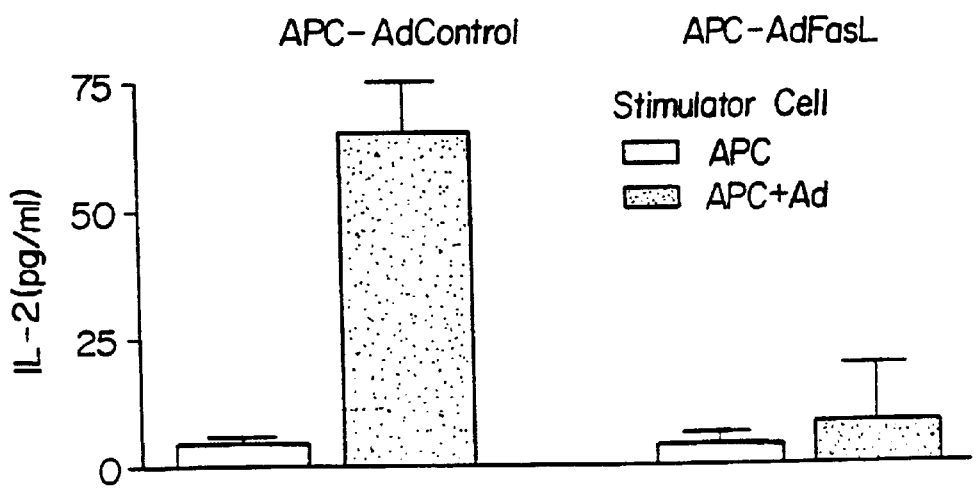
FIG. 6. IL-2 induction by spleen cells from tolerized B6+/+ mice. $10^6$ of the APC-AdFasL or APC-AdControl cells are transferred to B6+/+ mice. The spleen cells are incubated for 24 hours with APCs that were uninfected, or infected with adenovirus, and irratiated. Levels of IL-2 in the supernatant is determined by ELISA.
Figure 7:
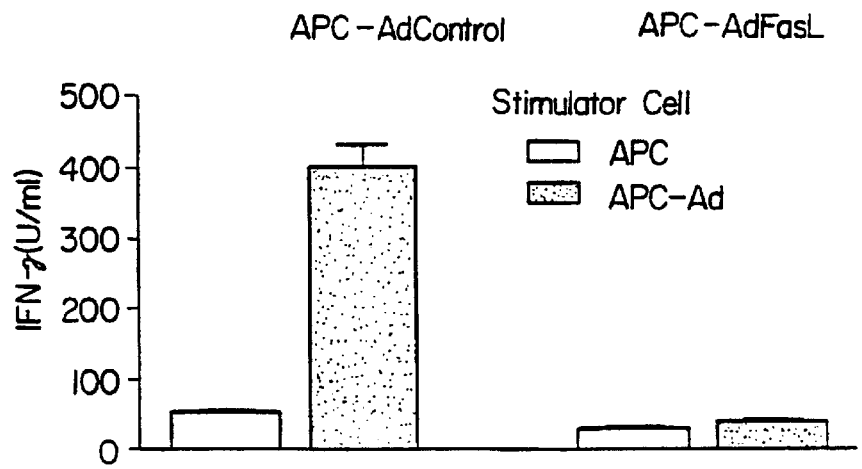
FIG. 7. IFN-gamma induction by spleen cells from B6 1pr/1pr mice. $10^6$ of the 1pr APC-AdFasL or APC-AdControl cells are transferred to B6-1pr/1pr mice. The spleen cells were incubated for 24 hours with APCs that are uninfected, or infected with adenovirus, and irratiated. Levels of IFN-γ in the supernatant is determined by ELISA.

Fas expression in recipient C57BL/6 mice is required for tolerance induction since spleen cells from B6-lpr/lpr mice produced high levels of IFN-γ and IL-2 despite being tolerized with APC-AdFasL (FIGS. 6, 7).

Example 19
Decreased T-cell Expansion in APC-AdFasL Treated Mice.

B6+/+ mice were treated with APC-AdFasL or APC-AdControl every 3 days for 5 doses, and then all treated mice were i.v. challenged with AdCMVlacZ (1×10$^{10}$ pfu). Three days later, frozen sections of spleen from naive mice, control APC treated mice, FasL APC treated mice and were stained with anti-CD3 antibody using a standard ABC technique. There was no expansion of CD3$^+$ T-cells in tolerized mice spleen, whereas mice treated with control APCs resulted in clonal expansion in spleen after challenge.

Example 20
APC-AdFasL Induces Specific Tolerance to Adenovirus.

Figure 8:
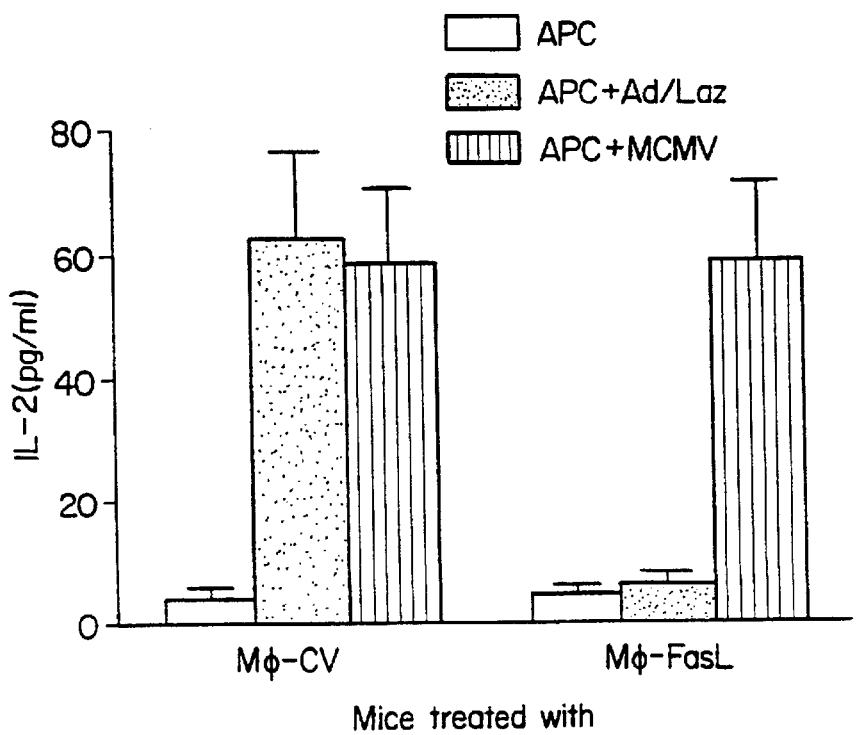
FIG. 8. Ad/FasL APCs induces specific T-cell tolerance to adenovirus. C57BL/6-+/+ mice (5 mice/group) are treated with either C57BL/6-+/+ mice (5 mice/group) are treated with APC-AdFasL or APC-AdControl (Mφ-CV). Seven days later, mice are challenged in vivo with either AdCMVLacZ or mouse cytomegalovirus (MCMV). After an additional 7 days, splenic T-cells are stimulated in vitro with APCs alone, or APCs infected with MCMV or AdCMV-LacZ. IL-2 production in the supernatants was determined by ELISA 48 hours later.

To determine if T-cell tolerance induced by Ad/FasL expressing APCs is specific for adenoviral vector rather than a general immune suppression to viral infection, the T-cell response by APC-AdFasL and APC-AdControl tolerized mice to an irrelevant viral infection is measured. B6+/+ mice are treated with APC-AdFasL as described above for induction of tolerance, and then challenged 7 days later with either adenovirus or mouse cytomegalovirus (MCMV). Although there is a reduction of T-cell response to adenoviral vector, the T-cell response to MCMV is not impaired as demonstrated by the comparable levels of IL-2 produced by the T-cells from both control and FasL APC treated mice (FIG. 8).

Example 21
Fas Ligand Expressing Adenovirus (Ad/FasL-βGal) Provides Both Systemic Immune Tolerance to Ad Transfected APCs and Confers Privilege on Cells That are Transfected With the Ad/FasL-βGal.

APCs transfected with Fas ligand induce specific apoptosis and specific T-cell tolerance to antigens both in vitro and in vivo. This is observed using a macrophage cell line derived from Fas-deficient C57BL/6(B6)-lpr/lpr mice that are transiently transfected with Fas ligand, and then injected into mice of a different MHC. In addition, macrophages co-infected with Fas ligand and viral vector are highly efficient presenters of viral vector antigens and Fas ligand. This results in antigen-specific apoptosis of vector-reactive T-cells. Transfection of Fas ligand into a β-islet cell line also confers immune privilege on the host β-islet-reactive T-cells and prevention of diabetes where the vector is adenovirus. These results show that muscle cells infected with Ad and co-transfected with Fas ligand created an immune privileged site in which the adenovirus is not capable of inducing an immune response.

Example 22
APCs Transfected With Fas Ligand Induce Apoptosis and Specific T-cell Tolerance to Antigens in Vitro and in Vivo.

An APC line derived by short-term culture of peritoneal macrophages from Fas mutant B6-lpr/lpr mice does not express Fas, but expressed MHC class II IA$^b$, MHC class I H-2D$^b$ antigens (FIGS. 9a, 9b), Mac-1, and Fc-γ receptor (data not shown). Significant levels of the B7 costimulatory molecule are expressed on 50% of the cells (FIG. 9c). This cell line is transfected with a eukaryotic expression vector (pcDNAIII) containing the full-length murine Fas ligand and selected using G418. APCs transfected with Fas ligand (APC-FL), but not control vector (APC-CV), exhibit high Fas ligand activity (FIG. 9d). APC-CV cells are capable of presenting alloantigen as the γ-irradiated cells induced a proliferative responses in co-cultured splenic H-2$^k$ T-cells (MRL-+/+ or MRL-lpr/lpr) (FIG. 9e). APC-FasL cells are capable of presenting alloantigen and induce a proliferative response if the responding T-cells are obtained from MRL-lpr/lpr mice, which do not express Fas. However, presentation of antigen by APCs that express Fas ligand to T-cells that express Fas antigen, obtained from MRL-+/+ mice, abrogated the proliferative response. Thus, in the present invention, presentation of antigen by APCs that express Fas ligand induces tolerance of the APCs-positive responding T-cells.

Example 23
Induction of Allogeneic T-cell Tolerance by Fas Ligand Expressing APCs.

4-wk-old of MRL-+/+ and -1pr/1pr mice are injected i.v. with macrophages ($2\times10^5$) transfected with Fas ligand or control vector every 3 d for 6 times. On d 3 of the final injection, splenic T-cells are isolated from treated mice and cultured under various stimulatory conditions. $5\times10^5$ T-cells are cultured with $2\times10^5$ γ-irradiated total spleen cells from B6+/+ mice (FIG. 10a). $5\times10^5$ T-cells are cultured with $2\times10^5$ γ-irradiated total spleen cells from BALB/c mice (FIG. 10b). $5\times10^5$ T-cells are cultured with 5 mg/ml of anti-CD3 antibody (FIG. 10c). T-cell proliferation is determined by incorporation of [$^3$H]-thymidine at 24, 48, 72 and 96 hours.

Example 24
Antigen-specific Clonal Deletion of the T-cells Induced by Fas Ligand Expressing APCs in H-2D$^b$/HY Reactive TCR Transgenic Mice.

Figure 11A:
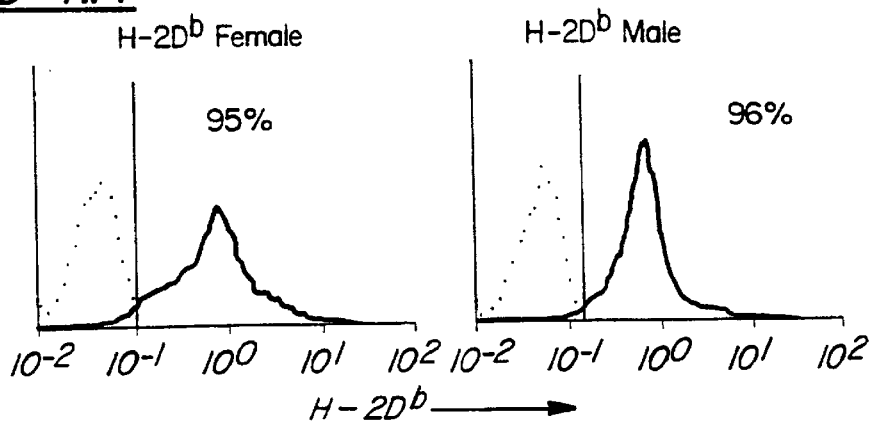
FIGS. 11A–11C. Antigen-specific clonal deletion of the T-cells induced by Fas ligand expressing APCs in H-2D$^b$/HY reactive TCR transgenic mice. (a) Expression of H-2D$^b$ is determined as described above and analyzed by flow cytometric analysis. (b) Fas ligand activity is assayed by specific lysis of A20 target cells at the indicated E/T ratio as described in FIG. 9. (c) The CD4 CD8 T-cells ($2 \times 10^6$) from B6-1pr/1pr female or male mice are injected every 3 d for 3 times into female, TCR transgenic D$^b$/HY -+/+ and -1pr mice. To demonstrate the requirement for FAS ligand in induction of T-cell tolerance, identical tolerizing experiments are carried out by co-injection with 100 mg of purlfied mouse Fas-Ig fusion protein capable of neutralizing Fas ligand in vivo. At the end of 12 d, $5 \times 10^5$ spleen T-cells are stimulated with 5 mg/ml of anti-CD3 or anti-clonotypic monoclonal antibody (M33), or with $2 \times 10^5$ irradiated H-2D$^b$/HY stimulator cells. The error bars indicate the mean ±SEM for 3 mice analyzed separately in triplicate assays.
Figure 11B:
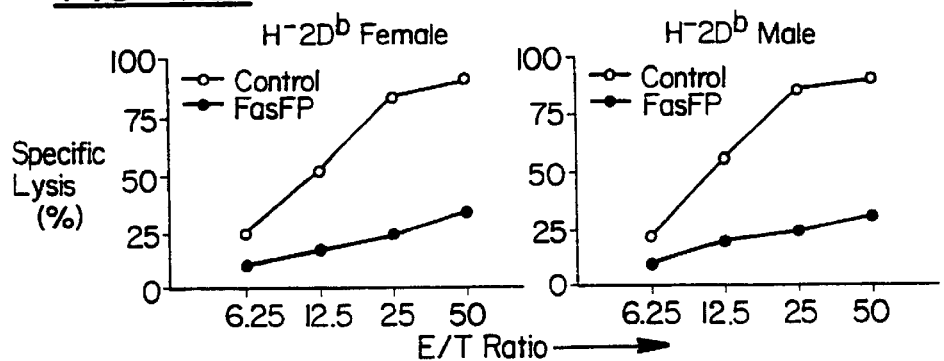
Figure 11C:
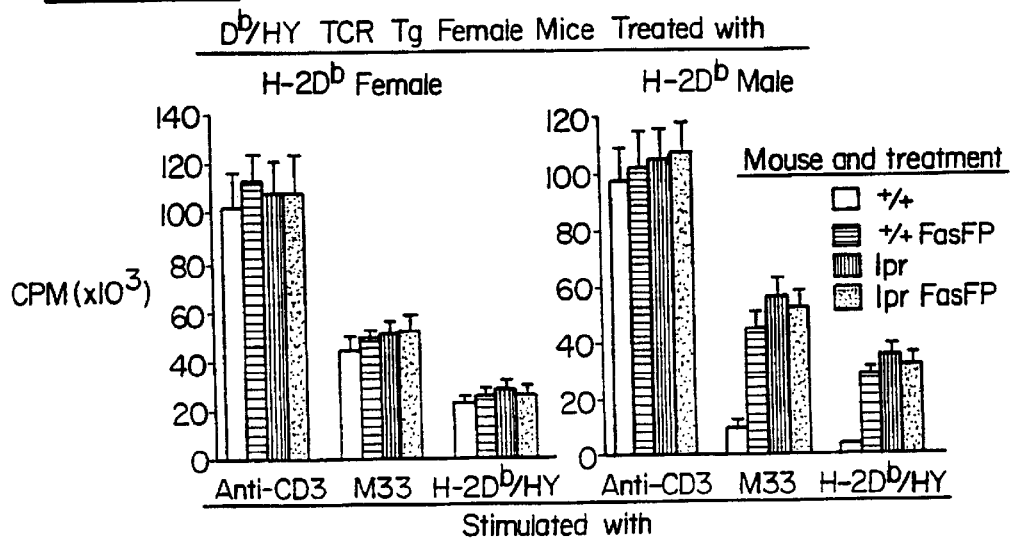

The ability of APCs that express Fas-ligand to mediate clonal deletion of antigen-specific T-cells is directly tested in female, T-cell receptor (TCR) transgenic, H-2D$^b$/HY-reactive mice. In these mice, the majority of peripheral CD8$^+$ T-cells bear the transgenic TCR and are reactive with the male HY antigen presented in the context of the H-2D$^b$ antigen. To obtain cells that bear H-2D$^b$, HY antigen and high levels of Fas ligand but not Fas, CD4$^-$CD8$^-$ T-cells are isolated from the peripheral lymph nodes of 5-month-old, male, B6-lpr/lpr mice. CD4$^-$CD8$^-$ T-cells isolated from 5-month-old, female, B6-lpr/lpr mice are used as controls in which the HY antigen is not expressed. The CD4$^-$CD8$^-$ T-cells obtained from both male and female B6-lpr/lpr mice expressed high levels of H-2D$^b$ antigen (FIG. 11a). The Fas ligand activity of the CD4$^-$CD8$^-$ T-cells is high and results in specific inhibition of this release by soluble Fas-Ig fusion protein (FIG. 11b). Alloantigen-specific T-cell tolerance was analyzed after i.v. injection of $1\times10^6$ CD4$^-$CD8$^-$ T-cells from either male or female mice into 4-wk-old, female, TCR transgenic +/+ or 1pr/1pr mice. T-cells from female, TCR transgenic +/+ mice treated with Fas ligand $^+$HY$^+$ and male cells exhibited a decreased proliferative response upon stimulation with either H-2D$^b$/HY spleen cells or crosslinking with the M33 anti-clonotypic TCR antibody, but not anti-CD3. Fas ligand-positive cells derived from H-2D$^b$ female mice had no effect on the H-2D$^b$/HY reactivity of recipient T-cells in TCR transgenic female mice. Comparable levels of T-cell proliferation were observed in response to stimulation with anti-CD3, M33 antibody, or H-2D$^b$/HY cells when the TCR transgenic female mice were treated with CD4$^-$CD8$^-$ T-cells of female mice (FIG. 11c). These results indicate that the decreased response requires the presence of the H-2D$^b$/HY antigen on the APCs and is specific for H-2D$^b$/HY reactive T-cells as there was a normnal response to crosslinking with anti-CD3.

Example 25
Tolerance Induction due to Fas-mediated Deletion of H-2D$^b$/HY Reactive CD8$^+$ T-cells.

Figure 12A:
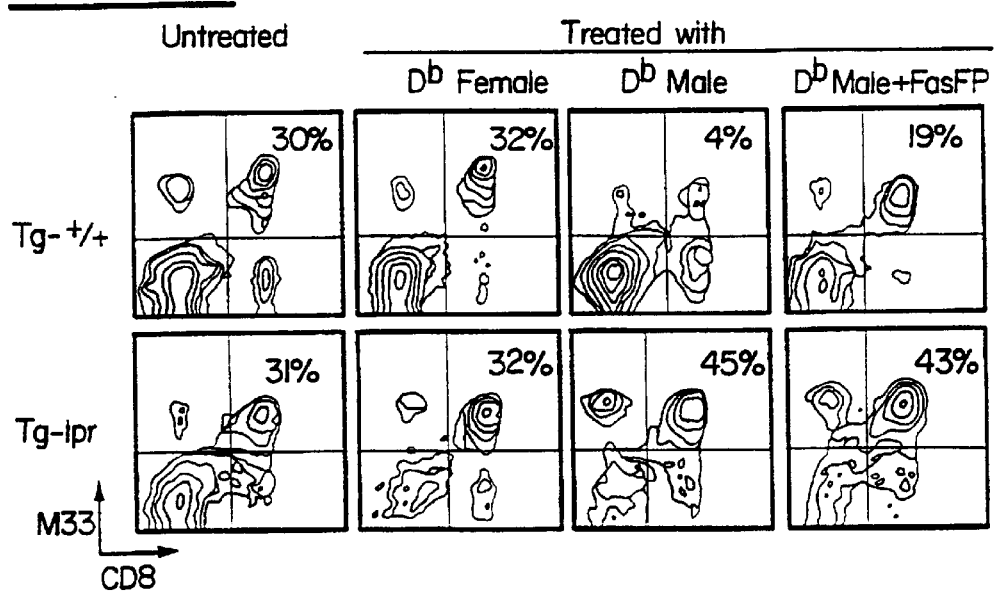
FIGS. 12A–12C. Tolerance induction due to Fas-mediated deletion of M33$^+$CD8$^+$ T-cells. (a) Expression of M33, CD8, and Fas on the T-cells in the PLN is determined by 3-color flow cytometric analysis. $1 \times 10^6$ total PLN cells are stained with biotin-conjugated M33, then with FITC-conjugated anti-CD8 and PE-conjugated anti-Fas (PharMingen). 10,000 viable lymphocytes were analyzed by FACScan. Two-color contour plots of CD8 and M33 are shown, and the percentage of M33$^+$CD8$^+$ T-cells multiplied by the total number of spleen cells. The error bars indicate the mean ±SEM for 3 mice analyzed. (b) Fas expression on the M33$^+$CD8$^+$ cells. (c) The M33$^+$CD8$^-$ cells are gated and the histograms of Fas are shown. The percentage of Fas expression on the gated M33$^+$CD8$^+$ T-cells is indicated.
Figure 12B:
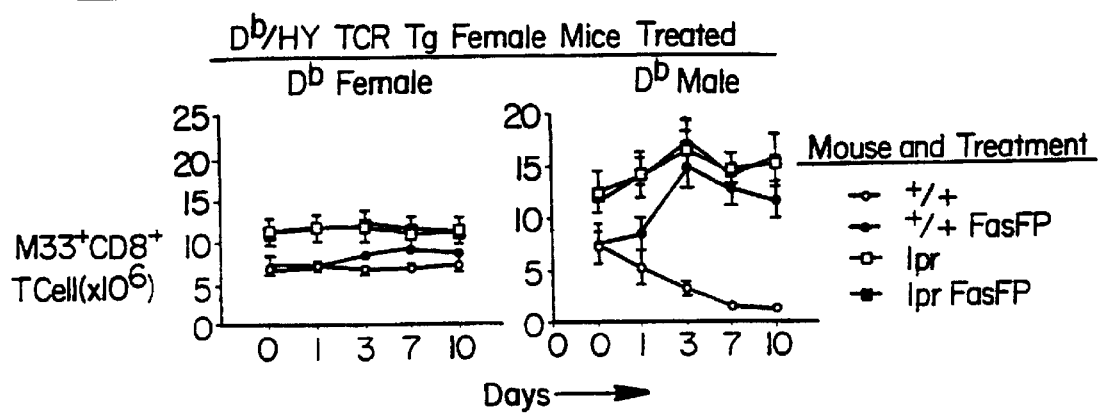
Figure 12C:
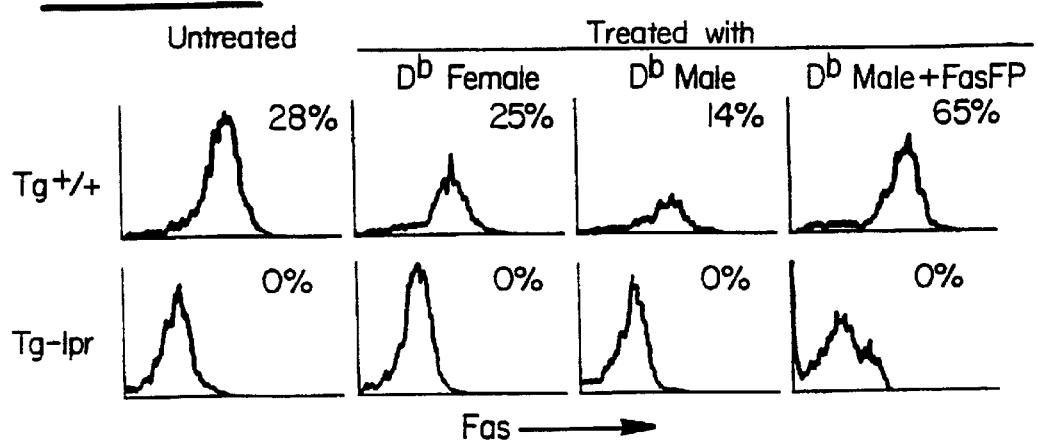

Clonal deletion of H-2D$^b$/HY cells is examined by analyzing the numbers of H-2D$^b$/HY reactive CD8$^+$ T-cells in the female TCR transgenic mice using the anti-clonotypic mAb M33. Tolerance induction is carried out as described above and the numbers of M33$^-$CD8$^-$ T-cells in the peripheral lymph node (FIG. 12a) and spleen (FIG. 12b) cells are deterrnined. In untreated, female, transgenic +/+ and lpr/lpr mice, approx. 30% of the PLN cells were M33$^+$CD8$^+$ T-cells and this percentage is not altered by treatment with female H-2D$^b$ cells lacking HY antigen (FIG. 12a). After tolerance induction in female, TCR transgenic, +/+ mice by Fas ligand-positive H-2D$^b$/HY cells, however, only 4% of PLN cells are M33$^+$ and CD8$^+$. This depletion of M33$^+$CD8$^+$ T-cells is inhibited significantly by Fas-Ig treatment in that 19% of the cells are M33$^+$CD8$^+$. Thus, induction of tolerance by Fas ligand expressing APCs is associated with Fas ligand-mediated clonal deletion of antigen-specific T-cells that recognize the antigen presented by the APCs. Time-course analysis of the deletion of M33$^+$CD8$^+$ T-cells in the spleen showed that the depletion commenced as early as 24 h after treatment in the female TCR transgenic +/+ mice that received Fas ligand-positive H-2D$^b$/HY cells and continued during the 10-d period of the treatment. Fas-Ig effectively inhibited the deletion in the TCR transgenic +/+ mice, which further supports the role of Fas ligand expression on the APCs in clonal deletion. Fas expression also is analyzed in M33$^+$CD8$^+$ PLN T-cells in the female TCR transgenic lpr/lprmice did not express Fas antigen regardless of treatment. Fas expression on M33$^+$CD8$^+$ T-cells expressed low levels of Fas (14%), whereas additional treatment with Fas-Ig led to the majority of M33$^-$CD8$^-$ T-cells being deleted by Fas ligand expressing APCs.

Example 26
Inhibition of Insulitis in NOD Mice Using a Synegeic β-islet Cell Line That Expresses Fas Ligand to Induce T-cell Tolerance.

Figure 13B:
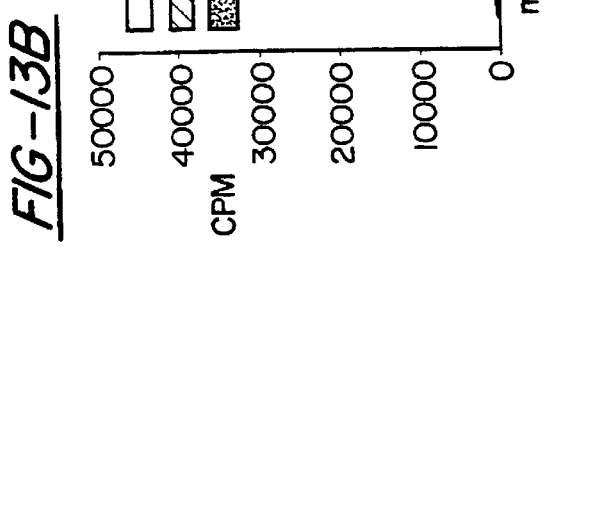
FIGS. 13A–13C. Fas ligand expressing β islet cells induce specific T-cell tolerance. (a) NIT-1 cells are transfected with pcDNAIII vector containing Fas ligand gene (NIT-1/FL) or empty vector (NIT-1/Ctl), and selected with G418. Fas ligand activity is measured by a [$^{51}$Cr] release assay. (b) 6-wk-old female NOD mice are i.p. injected with $5 \times 10^5$ NIT-1/FL or NIT-1/Ctl once. Splenic T-cells are isolated 2 wk later and co-cultured with irradiated NIT-1 cells. Proliferative T-cell response is determined by [$^3$H]-thymidine incorporation after 72 h culture. (c) The splenic T-cells from Example 25 are incubated with [$^{51}$Cr]-labeled NIT-1 cells at indicated E/T ratios, specific release is determined at 12 h.
Figure 13C:
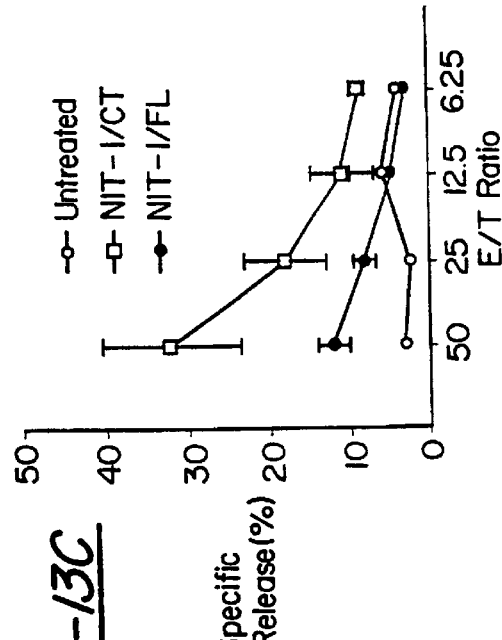
Figure 13A:
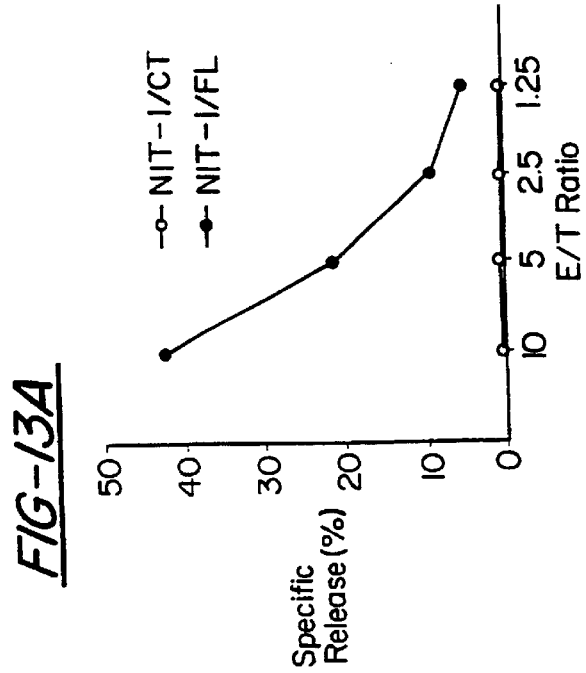
Figure 15:
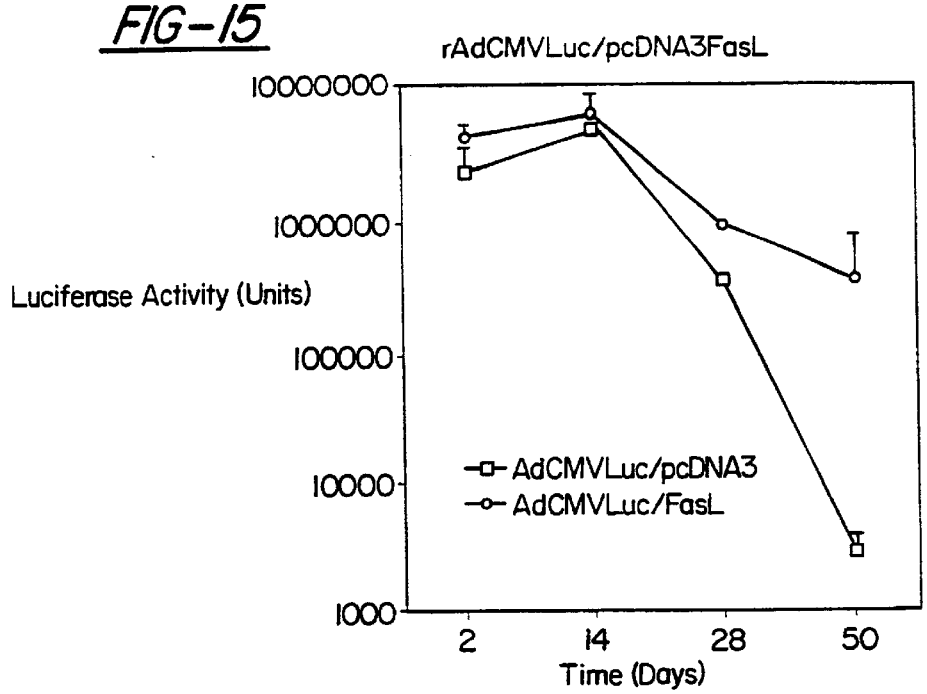
FIG. 15. Prolonged expression of Ad/Luc in muscle co-transfected with pFasL. Tongue muscle of mice (5 mice/group) were analyzed at different time points for luciferase production. There was increased production of luciferase in muscle cells injected with adenovirus plus FasL compared to muscle injected with adenovirus and control empty vector.

NOD mice develop spontaneous insulitis and diabetes due to a T-cell-mediated autoimmune response to self-β cells. The syngeneic β cell line, NIT-1, is used as the APC for Fas ligand expression. NIT-1 cells do not express Fas antigen and do not undergo either anti-Fas antibody or Fas ligand mediated apoptosis (data not shown). This cell line is transfected with an expression vector containing Fas ligand mediated apoptosis (data not shown). This cell ine is transfected with an expression vector containing Fas ligand (pcDNAIII) as described in Example 9. Fas ligand transfected, but not control, cells expressed functional Fas ligand (FIG. 13a). 6-wk-old, female, NOD mice are injected once with $5\times10^5$ Fas ligand expressing, or control, NIT-1 cells. Seven d later, the splenic T-cells are isolated from treated NOD mice and co-cultured with irradiated NIT-1 cells. There are increased T-cell proliferative and cytotoxic responses in NOD mice treated with control NIT-1 cells (FIGS. 13b,c). In contrast, NOD mice treated with Fas ligand expressing NIT-1 cells only exhibit a minimal increase in response compared with the untreated control. 100% of NOD mice that received no treatment or treatment with NIT-1/CV developed insulitis, and 100% of islets from each individual mouse are involved. In contrast, only 1 of 3 mice receiving NIT-1/FasL developed minor insulitis, with only 10% of islets involved (FIG. 14).

Example 27
Inhibition of Insulitis in Nod Mice Using NIT-1-AdFasL as a Syngenic β Islet Cell to Induce T-cell Tolerance to an Ad Vector.

The procedure of Example 25 is repeated with the expression vector of Example 14 substituted therein. NIT-1-Ad control treated mice develop insulitis involving 100% of islet cells of individual mice. NIT-1-AdFasL treated mice did not develop insulitis.

Example 28
Transfection With Fas Ligand and Adenovirus Results in High Expression of β-Gal in Macrophages.

The polylysine method is used for targeting Fas ligand and Ad to APC via the receptor-mediated endocytosis pathway (49–51, 68, 69). It is important to link Ad to molecular conjugates, and at the same time preserve both the binding and endosome disruption capabilities of the virus. The linkage is accomplished by conjugating a molecular antibody against a foreign epitope on the adenovirus hexon protein to the polylysine-protein complex. For this purpose a chimeric adenovirus containing a foreign epitope in the surface region of its hexon protein is constructed. The loop region of the hexon protein is a useful foreign epitope expression region.

Example 29
Creation of an Immune-privileged Site for Prolonged Expression of the Adenovirus Gene Product Using Co-expression of FasL and Adenovirus in Muscle.

$10^9$ adenovirus is co-injected into mouse muscle tissue with 5 μg of purified FasL DNA under the regulation of the CMV promoter (pFasL), or with identical control plasmid DNA which does not express Fas ligand. FasL production by adenovirus confers a high level of specific immunity to the adenovirus, prevent immune elimination of cells expressing the adenovirus, and result in prolonged expression of the adenovirus gene product. These results are consistent with previous studies showing that FasL production in muscle cells created an immune privileged site (42).

Example 30
Modification of Viral Tropism to Allow High Efficiency Targeting to Macrophages.

In addition to the in vitro infection and tolerance induction by Ad/FasL, in vivo infection by an Ad/FasL virus is operative. A FasL Tg mouse which overexpresses FasL specifically in T-cells without cytotoxicity is used (70). Similar techniques direct Ad/FasL for high transfection of APCs in vivo (macrophages) by targeting adenovirus to the macrophage mannose receptor. This is accomplished using a synthetic molecular conjugate consisting of a mannosylated polylysine protein combined with the adenovirus fiber/knob protein. A mannosylated polylysine has been demonstrated to bind to the macrophage mannose receptor and lead to high efficiency transfection of DNA complexes into islet cells (71, 72). Modification of adenovirus tropism uses the methods detailed in U.S. Provisional Patent Application No. 60/054,112 for modification of the adenovirus knob/fiber protein to include a 10 amino acid polypeptide capable of binding E-selectin and targeting adenovirus to inflamed sites in the synovium and also using an anti-adenovirus sFv/IL-2 fusion protein to direct adenovirus tropism to T-cells.

Example 31
Production of an Adenovirus-infected, Fas Ligand Expressing Macrophage for Induction of Tolerance to Adenovirus.

The APC line of Example 22 expresses high level of MHC class I and II antigen, B7 and Fas ligand. This macrophage cell line express high levels of $H-2D^b$ and $I-A^b$ as well as B7 upon the stimulation with LPS or IFN-γ. This cell lines does not express Fas, exhibits low levels of Fas ligand activity, and has been transfected with a CMV promoter/FasL construct to produce a stable transfected macrophage cell line which expresses FasL. This cell line can also be infected with Ad by known techniques to allow expression of adenovirus antigens and gene products.

Example 32
Analysis of Tolerance to Ad/Fas Ligand.

Tolerance to adenovirus is analyzed using a macrophage cell line that stably expresses Fas ligand (APC-FL), such as that of Example 22, and are infected with the adenovirus by intravenous (i.v.) or intranasal (i.n.) injection to induce tolerance. Tolerance is analyzed at d 2, 7, 14, 28, and 56 after injection of $5 \times 10^6$ Ad-APC-FL. Mice are bled by retroorbital sinus puncture for analysis of antibody titer to adenovirus.

Example 33
Determination of Tolerance to Ad.

Single cell suspensions of spleen and lung are prepared for determination of the proliferative response upon co-culture with normal, irradiated $H-2^b$ Ad-APC. T-cells tolerance are evaluated by [$^3$H]-thymidine incorporation to measure the T-cell proliferative response, BrdU incorporation, and flow cytometric analysis of BrdU-positive T-cells to determine the frequency of proliferative T-cells, and 7AAD three color flow cytometric analysis to determine apoptosis of the T-cells. The level of IL-2 in the culture supernatants is also measured to determine T-cell activation. A similar technique is used to test to determine if cytotoxic $CD8^+$ T-cells are toleralized or deleted from the spleen in vivo. The $CD8^+$ T-cells are tested for their ability to lyse chromium-labeled Ad-APC. Purified T-cells are isolated as described in reference to FIG. 10. A suitable effector: target (E:T) ratio of $CD8^+$ T-cells to chromium-labeled, adenovirus-pulsed macrophage target cells is thereby obtained.

Example 34
Construction of an Adenovirus Producing Fas Ligand.

Figure 16:
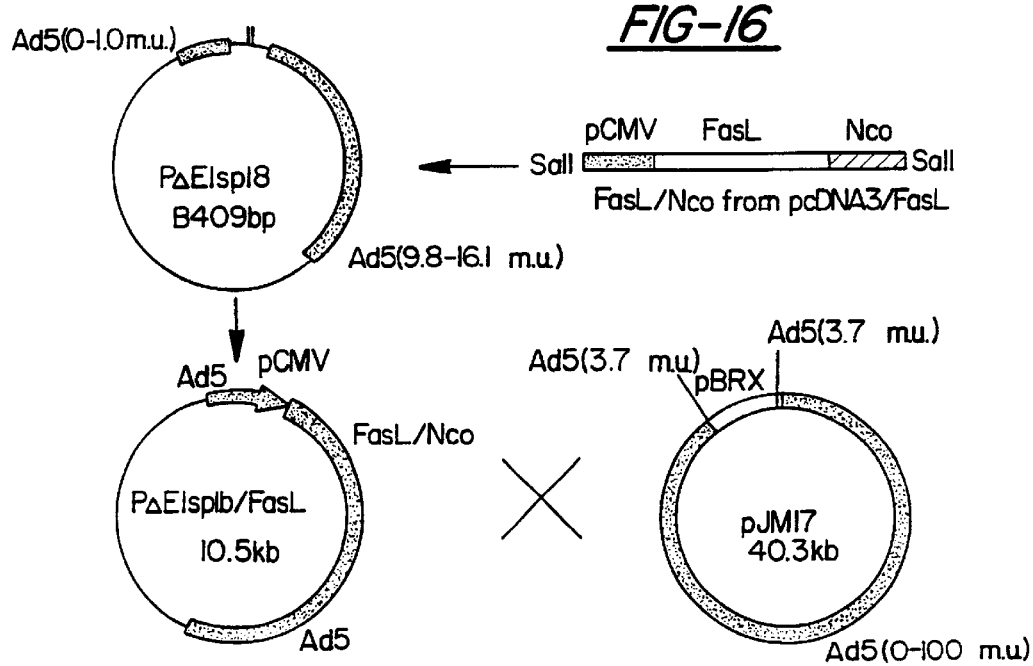
FIG. 16. Construction of pΔE1sp1b/FL and PSM17. Production of pΔE1sp1b/FasL. Shown is a 10.5 kb vector that contains Ad from 0 map units to 1 map unit, the CMV promoter, full length Fas ligand and a 0.4 kb SV40 polyA tail. This shuttle vector was combined with the 40.3 kb pJM17 vector containing the adenovirus genome –ΔE1 and also contains an origin replication and an ampicillan-resistant site.

First, a full length 1114bp murine Fas ligand cDNA clone is obtained by conventional methods (73–75). Second, this Fas ligand clone is used to produce the Ad/FasL vector (FIG. 16). Third, this clone has undergone recombination with the adenovirus genome in 293 cells. This construct and variations of this construct are used in the present invention. The Fas ligand cDNA clone is introduced into the pΔE1sp1b shuttle vector. To produce recombinant adenovirus, this DNA is co-transfected into weakly $Fas^+293$ cells. A total of 6 transfections are carried out using 3 different transfection methods including: lipofectin, dotap, and the calcium chloride precipitation method. Under all conditions, the majority of the transfected 293 cells undergo apoptosis within 24 h, whereas minimal apoptosis occurs after transfection of 293 cells with the control shuttle vector.

Example 35
Production of pΔE1sp1Bloxp/FasL:.

Figure 17:
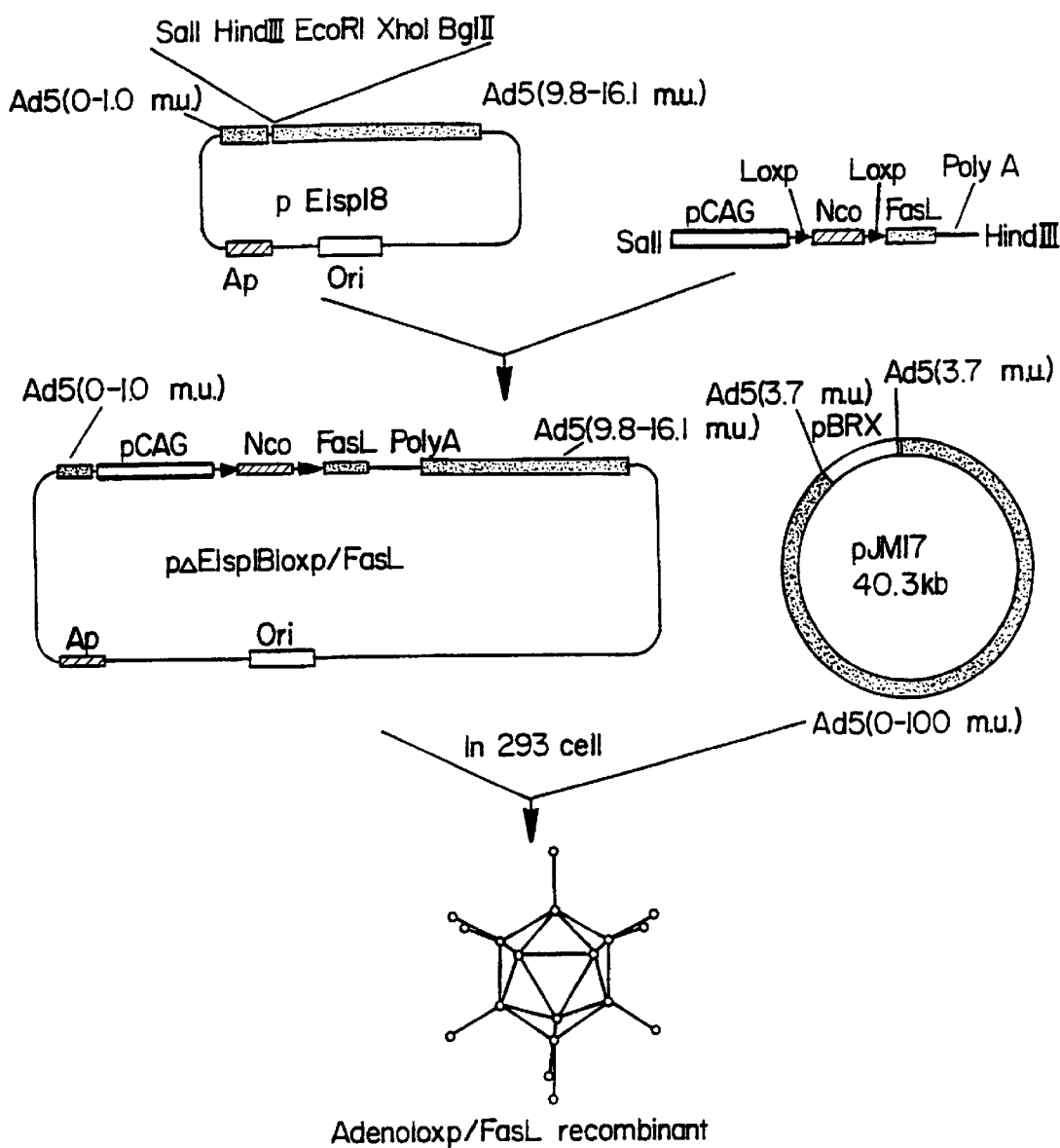
FIG. 17. Production of pΔE1sp1Bloxp/FasL. A 10.4 kb shuttle vector containing the fragment of adenovirus from 0 map unit to 1 map unit is followed by the 0.7 kb CMV promoter. This is followed by 2 LOXP sites separated by a 2 kb stuffer fragment plus a 0.3 kb bovine growth hormone polyA tail. The full-length 0.9 kb Fas ligand is cloned downstream from the stuffer fragmgent which is followed by an SV40 PolyA tail and by the 9.8–16.1 map units of adenovirus.

A Fas ligand expressing recombinant adenovirus, denoted as AdLOXP/FasL recombinant virus is shown in FIG. 17. The pΔE1sp1Bloxp/Fas shuttle vector is co-transfected with pJM17 to produce the AdLOXP/FasL. The AdLOXP/FasL is co-infected with the Ad/CRE recombinant adenovirus. The CRE excises the LOXP sites placing FasL under the control of the CMV promoter resulting in high levels of expression of FasL. As outlined in the detailed description of the invention, AdLOXP/FasL does not induce toxicity in the 293 cells. The AdLOXP/FasL adenovirus is combined with the Ad/CRE recombinant adenovirus. The CRE protein has been well studied and is demonstrated to be able to excise the LOXP sites which in the present invention construct results in the production of FasL under the CMV promoter. This system was first heavily utilized for production of trrnsgenic mice. It has applied by several investigators for adenovirus recombination (73–75). These viruses can be co-infected into any cell, such as macrophages used herein with high efficiency.

Example 36
Confirmation That the Macrophage Cell line Transfected With the Adenovirus Expresses LacZ and Fas Ligand.

Macrophages are transfected with the recombinant adenovirus. Lac z expression is confirmed by β-galactosidase staining as described in Example 8. After gene therapy, mice are analyzed at different time courses for expression of the lacZ marker gene in the lung and liver. Fas ligand expression is confirmed by ability of the transfected macrophages to induce apoptosis of $^5$Cr labeled and Fas sensitive cell line A20 as per Example 5. These experiments are carried out with and without the presence of a soluble Fas (sFas) capable of neutralizing Fas ligand activity to demonstrate that cytotoxicity is specific for Fas ligand.

Example 37
Treatment of a Lung Disease With AdCF/FasL Transfected Into APCs.

The CF gene is ligated into the EcoRV site of the Ad shuttle vector of FIG. 16 so as to be under the control of the regulatory element. The CF modified vector, Ad Shuttle CF is co-transfected with pJM17 to produce recombinant AdCF. To produce FasL, this is co-infected with the AdLOXP FasL and AxCanCre. These three viruses will be co-administered intra-nasally into the airways of 6 week old, female bleomycin—IPF mice. On day 7 after the injection, the mice are challenged with AdCF. The mice so treated are tolerant of the CF gene therapy vector 7 days after challenge.

Example 38
Treatment of a Lung Disease With AdPI/FasL Transfected Into APCs.

The protease inhibitor (PI) gene is ligated into the EcoRV site of the Ad shuttle vector of FIG. 16 so as to be under the control of the regulatory element. The PI modified vector, Ad Shuttle PI is co-transfected with pJM17 to produce recombinant AdPI. To produce FasL, this is co-infected with the AdLOXP FasL and AxCanCre. These three viruses will be cadministered intra-nasally into the airways of 6 week old, female bleomycin—IPF mice. On day 7 after the injection, the mice are challenged with ADPI. The mice so treated are tolerant of the PI gene therapy vector 7 days after challenge.

Example 39
Treatment of Hemophilia With AdF8/FasL Transfected in APCs.

The factor VIII gene is ligated into the EcoRV site of the pJM 17 vector of FIG. 16 so as to be under the control of the regulatory element. The PI modified vector, Ad Shuttle Factor VIII is co-transfected with pJM 17 to produce recombinant Ad Factor VIII. To produce FasL, this is co-infected with the Ad LOXP FasL and AxCanCre. These three viruses will be co-administered intra-nasally into the airways of 6 week old, female bleomycin—IPF mice. On day 7 after the injection, the mice are challenged with Ad Factor VIII. The mice so treated are tolerant of the Factor VIII gene therapy vector 7 days after challenge.

Example 40
Determine the Expression of Fas Ligand and Ad/p-gal in Vivo at Different Time Points After Infection in Vivo in Tolerized and non-tolerized Mice.

Detailed analysis of expression of Fas ligand RNA and protein, viral RNA and protein, and β-gal is carried out at different time point and under different conditions of tolerance induction involves analysis of tissue sections using immunohistochemical staining for Fas, β-Gal. Tissue sections are also analyzed for in-situ expression by RT-PCR and for apoptosis by the tunel method. The phenotype of T-cell and macrophages in lymphoid organs and lung is determined by flow cytometry analysis. Fas ligand expression by single cell suspension is determined by 1) Cr release assay of Fas apoptosis sensitive target cells, 2) frequency analysis by single cell Fas ligand PCR.

Example 41
Mechanism to Abolish Fas Expression of Fas Apoptosis Signaling by the Cell That is Infected With the Ad/FasL-gene Therapy Vector.

To abolish cell surface Fas expression, it is sufficient to prevent Fas apoptosis signaling, since it is well established that Fas expression does not necessarily correlate with Fas apoptosis signaling (76–81). The analysis of Fas-apoptosis signaling and inhibition of this by IL-1β converting enzyme family members and also inhibitors of HCP are useful in testing abolition. The will be accomplished by incorporating both Fas and known inhibitory proteins of Fas apoptosis into modified Ad virus. A specific construct capable of expressing Fas ligand safely and at the same time protect the Fas ligand expressing cell from autocrine-mediated apoptosis includes both FasL and fragments of IL-1β or repeats of the peptide sequence the CPP32/Yama inhibitor DEVD-CHO, the ICE inhibitor YVAD-CHO which inhibit ICE and CPP32 and prevent Fas-mediated apoptosis in different cells, and Crm A, which block the cas pase pathway (81). These experiments show the ablation of the endogenous tropism of the adenovirus and the addition novel tropism of the adenovinis to antigen presenting cells. Highly efficient ablation of endogenous tropism is important for using the immune modulating strategies proposed of the present invention.

Any patents or publications mentioned in this specification are indicative of the levels of those skilled in the art to which the invention pertains. These patents and publications are herein incorporated by reference to the same extent as if each individual publication was specifically and individually indicated to be incorporated by reference.

TABLE 1

| | | Immune Response | | |
|---|---|---|---|---|
| Adenovirus Vector | Source of Spleen Cells | Proliferation | Cytotoxicity | Anti-adenovirus antibody |
| Adenovirus-Control Vector | B6-+/+ | 3$^+$ | 3$^+$ | 3$^+$ |
| Adenovirus-Control Vector | B6-lpr/lpr | 4$^+$ | 4$^+$ | 4$^+$ |
| Adenovirus-Fas Ligand | B6-+/+ | 0 | 0 | 0 |
| Adenovirus-Fas Ligand | B6-lpr/lpr | 4$^+$ | 4$^+$ | 4$^+$ |

Reference

1. Yang Y. et al. J. of Immunology. 155(5):2564–70, 1995.
2. Christ M. et al. Immunology Letters. 57(1–3):19–25, 1997.
3. Yang Y. et al. J. of Virology. 69(4):2004–15, 1995.
4. Gilgenkrantz H. et al. Human Gene Therapy. 6(10):1265–74, 1995.
5. Yang Y. et al. Proceedings of the National Academy of Sciences of the United States of America. 91(10):4407–11, 1994.
6. Juillard V. et al. European J. of Immunology. 25(12):3467–73, 1995.
7. Yang Y. et al. J. of Virology. 70(9):6370–7, 1996.
8. Schowalter D B. et al. Gene Therapy. 4(8):853–60, 1997.
9. Qin L. et al. Human Gene Therapy. 8(11):1365–74, 1997.
10. Guerette B. et al. Human Gene Therapy. 7(12):1455–63, 1996.
11. Zsengeller Z K. et al. Human Gene Therapy. 8(8):935–41, 1997.
12. Bellgrau D. et al. Nature 1995; 377:630–632.
13. French L E. et al. J Cell Biol.; 1996:335–343.
14. Lee J. et al. Endocrinology 1997; 138:2081–2088.
15. Griffith T S. et al. Immunity 1996; 5:7–16.
16. Watanabe-Fukunaga R. et al. Nature 1992;356:314–317.
17. Zhou T. et al. J. Exp Med 1992; 176:1063–1072.
18. Suda T. et al. Cell 75:1169–78, 1993.
19. Wu J. et al. Proc Natl Acad Sci U S A 1994; 91:2344–2348.
20. Suda T. et al. J Immunol. 154:3806–13, 1995.
21. Cheng J. et al. J Immunol. (In press), 1997.
22. Teng M N. et al. Clin Immunol Immunopath. 69:215–222, 1993.
23. Marsters S A. et al. J Biol Chem. 26:5747–5750, 1992.
24. Gilgenkrantz H. et al. Human Gene Therapy. 6:1265–1274, 1995.
25. Sawchuk S J. et al. Human Gene Therapy. 7:499–506, 1996.
26. Elshami A A. et al. Ann. Surg. 222:298–307; 1995.
27. DeMatteo R P. et al. Ann. Surg. 222:229–239, 1995.
28. Goldman M H. et al. Human Gene Therapy. 6:839–851, 1995.
29. Amalfitano A. et al. Proc Natl Acad Sci. 93:3352–3356, 1996.
30. Zepeda M. et al. Gene Therapy. 3(11):973–9, 1996.
31. Ilan Y. et al. J. of Clinical Investigation. 99(5):1098–106, 1997.
32. Bennett J. et al. Human Gene Therapy. 7(14):1763–9, 1996.
33. Muruve D A. et al. Transplantation. 64(3):542–6, 1997.
34. Sigalla J. et al. Human Gene Therapy. 8(13):1625–34, 1997.
35. J. Virol. 72:2483–2490, 1998.
36. J. Biol. Chem. 253:6551.
37. Nagata S. Science. 267:1449–56, 1995.
38. Mountz J D. et al. J. Immunol. 155:4829–4837, 1995.
39. Wu J. et al. Proc Natl Acad Sci USA. 91:2344–2348, 1994.
40. Zhou T. et al. Eur J Immunol. 24:1019–1025, 1994.
41. Watanabe-Fukunaga R. et al. Nature. 356:314–317, 1992.
42. Lau H T. et al. Science. 273:109–112, 1996.
43. Griffith T S. et al. Science. 270:1189–1192, 1995.
44. T. Zhou et al. (submitted)
45. Zhang H G. et al. J Virol. 72(3):2483–2490, 1998.
46. Michou A I. et al. Gene Therapy. 4(5):473–82, 1997.
47. Song W. et al. Human Gene Therapy. 8(10):1207–17, 1997.
48. Tripathy S K. et al. Nature Medicine. 2:545–550, 1996.
49. Michael S I. et al. J. Biol. Chem. 268:6866–9, 1993.
50. Gao L. Human Gene Therapy. 4:17–24, 1993.
51. Curiel D T. Progress in Medical Virology. 40:1–18, 1993.
52. Cotten M. et al. PNAS. 89:6094–8, 1992.
53. Schwarzenberger P. et al. Blood. 87:472–8, 1996.
54. Michael S I. et al. Gene Therapy. 2:660–8, 1995.
55. Batra R K. et al. Gene Therapy. 1:255–60, 1994.
56. Michael S I. et al. Gene Therapy. 1:223–32, 1994.
57. Garver R I Jr. et al. Gene Therapy. 1:46–50, 1994.
58. Wu K. et al. J. Biological Chemistry. 271:21323–30, 1996.
59. Ferkol T. et al. PNAS. 93:101–5, 1996.
60. Jiang W. et al. Nature. 375:151–5, 1995.
61. Clarke S. et al. PNAS. 93:1434–1438, 1996.
62. Phi van L. Biochem. J. 313:3944, 1996.
63. Dighe A S. et al. Immunity. 3:657–666, 1995.
64. Sawchuk S J. et al. Hum Gene Therapy. 7:499–506, 1996.
65. Mountz J D. et al. J Immunol 155:4829–4837, 1995.
66. Young et al. Anal. Biochem. 215:24–30,1993.
67. Zsengeller Z K. et al. Hum GeneTherapy. 6:457–467, 1995.
68. Deshane J. et al. Cancer Gene Therapy. 3:89–98, 1996.
69. Deshane J. et al. J. Clin. Invest. 96:2980–2989, 1995.
70. Cheng J. et al. J. Immunol. (submitted)
71. Ebbinghaus S W. et al. Gene Therapy. 3:287–297, 1996.
72. Saldeen J. et al. Diabetes. 45:1197–2203, 1996.
73. Choulika A. et al. J. Virology. 70:1792–1798, 1996.
74. Wang P. et al. Somatic Cell & Molecular Genetics. 21:429441, 1995.
75. Sakai K. et al. Biochem. Biophys. Res. Comm. 217:393–401, 1995.
76. Su X. et al. Immunity. 2:353–362, 1995.
77. Su X. et al. J. Immunol. 156:4198–4208, 1996.
78. Zhou T. et al. J. Exp. Med. 183:1879–92, 1996.
79. Mountz J D. et al. Journal of Clin. Immunol. 15:1–16, 1995.
80. Tatsuta T. et al. J. Immunol. 157:3949–3957, 1996.
81. Hasegawa J. et al. Cancer Res. 46:1713–8, 1996.

Various modifications of the present invention, in addition to those shown and described herein, will be apparent to those skilled in the art of the above description. Such modifications are also intended to fall within the scope of the appended claims.

What is claimed is:

1. A viral vector comprising:
   a transgene;
   a Fas ligand gene; and
   a gene expression control means for directing product synthesis of said transgene and said ligand gene in a host.

2. The vector of claim 1 wherein said vector is a recombinant adenovirus.

3. The vector of claim 1 wherein said vector is a recombinant adeno-associated virus.

4. The vector of claim 1 wherein said vector is a recombinant herpes virus.

5. The vector of claim 1 wherein said vector is selected from a group consisting of: adenovirus, adeno-associated virus and herpes virus.

6. The vector of claim 5 wherein said vector is replication defective.

7. The vector of claim 1 further comprising only non-pathogenic viral vector genes.

8. The vector of claim 1 wherein said Fas ligand gene codes for multimers of Fas ligand gene.

9. The vector of claim 1 wherein said Fas ligand gene is an apoptosis inducing Fas ligand gene.

10. The vector of claim 9 wherein said Fas ligand gene is selected from the group consisting of: a fragment, a truncant, and a multimer.

11. The vector of claim 1 wherein said gene expression control means comprises a promoter, an open reading frame and a signal sequence.

12. The vector of claim 11 further comprising an enhancer.

13. A viral vector comprising:
   a transgene;
   a viral vector gene that is expressed as an antigen on an infected host cell;
   a Fas ligand gene; and
   a gene expression control means for directing product synthesis of said transgene and said Fas ligand gene in a host.

14. The vector of claim 13 wherein said gene expression control means comprises a promoter, an open reading frame and a signal sequence.

15. The vector of claim 14 further comprising an enhancer.

16. The vector of claim 15 wherein said enhancer is a viral enhancer.

17. The vector of claim 13 wherein said vector is selected from the group consisting of: adenovirus, adeno-associated virus and herpes virus.

18. The vector of claim 13 wherein said vector is replication defective.

19. The vector of claim 13 further comprising only nonpathogenic viral vector genes.

20. A vector system for promoting T cell tolerance comprising:
   a first viral construct comprising:
   a nucleic acid sequence encoding a CRE recombinase;
   a gene expression control means for directing product synthesis of the nucleic acid sequence encoding a CRE recombinase;
   a viral gene expressed as an antigen on an infected host cell; and
   a second viral construct comprising:
   a loxp target sequence for a CRE recombinase;
   a nucleic acid sequence encoding a Fas ligand;
   a gene expression control means for directing product synthesis of the Fas ligand; and
   a viral gene expressed as an antigen on an infected host cell;
   wherein the Fas ligand is expressed when the first viral construct and the second viral construct are present together in a mammalian cell and wherein said equivalent promotes T cell apoptosis.

21. The vector system of claim 20 wherein the first and second viral constructs are each independently selected from the group consisting of: adenovirus, adeno-associated virus and herpes virus.

22. A mammalian cell comprising:
   a first viral vector construct comprising:
   a nucleic acid sequence encoding a CRE recombinase,
   a gene expression control means for directing product synthesis of the nucleic acid sequence encoding a CRE recombinase,
   a viral vector gene that is expressed as an antigen on an infected host cell; and
   a second viral vector construct comprising:
   a loxp target sequence,
   a nucleic acid sequence encoding a Fas ligand, wherein the Fas ligand promotes T cell apoptosis,
   a gene expression control means for directing product synthesis of the Fas ligand; and
   a viral vector gene that is expressed as an antigen on an infected host cell.

* * * * *

UNITED STATES PATENT AND TRADEMARK OFFICE
CERTIFICATE OF CORRECTION

PATENT NO. : 6,689,605 B1
DATED : February 10, 2004
INVENTOR(S) : John D. Mountz It is certified that error appears in the above-identified patent and that said Letters Patent is hereby corrected as shown below:

Column 3,
Line 24, "sites" should be replaced with -- site --.

Column 5,
Line 21, "supermatants" should be replaced with -- supernatants --.

Column 6,
Line 6, "purlfied" should be replaced with -- purified --.
Line 65, "fragmgent" should be replaced with -- fragment --.

Column 7,
Line 50, "Ad." should be replaced with -- Ad, --.

Column 10,
Lines 41 and 55, "also be employed" should be replaced with -- also emplyed --.

Column 11,
Line 6, "grft" should be replaced with -- graft --.
Line 29, "orelectroporation" should be replaced with -- or electroporation --.
Line 37, "adenovinis" should be replaced with -- adenovirus --.

Column 12,
Line 61, "oftolerance" should be replaced with -- of tolerance --.

Column 13,
Line 7, "long" should be replaced with -- lung --.
Line 23, "primary" should be replaced with -- primarily --.
Line 40, "cytoplasnmic" should be replaced with -- cytoplasmic --.

Column 14,
Line 15, "virus" should be replaced with -- viruses --.
Line 31, "continue to incubated" should be replaced with -- continue to be incubated --.

Column 15,
Line 23, "miin" should be replaced with -- min --.

Column 16,
Line 7, "ganrina" should be replaced with -- gamma --.
Line 27, "manu facturer's Smanual" should be replaced with -- manufacturer's manual --.

UNITED STATES PATENT AND TRADEMARK OFFICE
CERTIFICATE OF CORRECTION

PATENT NO. : 6,689,605 B1
DATED : February 10, 2004
INVENTOR(S) : John D. Mountz It is certified that error appears in the above-identified patent and that said Letters Patent is hereby corrected as shown below:

Column 17,
Line 42, "determnined" should be replaced with -- determined --.
Line 49, "supermate" should be replaced with -- supernate --.

Column 19,
Line 55, "normnal" should be replaced with -- normal --.
Line 65, "deterrnined" should be replaced with -- determined --.

Column 20,
Line 19, "lpr/lprmice" should be replaced with -- lpr/lpr mice --.
Line 35, "ine" should be replaced with -- line --.

Column 22,
Line 64, "trrnsgenic" should be replaced with -- transgenic --.

Column 23,
Line 39, "cadministered" should be replaced with -- co-administered --.

Column 24,
Line 34, "The" should be replaced with -- This --.
Line 45, "adenovinis" should be replaced with -- adenovirus --.

Signed and Sealed this

Sixth Day of September, 2005

JON W. DUDAS
*Director of the United States Patent and Trademark Office*